(12) United States Patent
Taylor et al.

(10) Patent No.: US 10,827,966 B2
(45) Date of Patent: Nov. 10, 2020

(54) FLUID COLLECTION DEVICE AND RELATED METHODS

(71) Applicant: OPKO Diagnostics, LLC, Woburn, MA (US)

(72) Inventors: Jason Taylor, Windham, NH (US); Hardeep Singh, Arlington, MA (US); Matthew Dirckx, Somerville, MA (US)

(73) Assignee: OPKO Diagnostics, LLC, Woburn, MA (US)

( * ) Notice: Subject to any disclaimer, the term of this patent is extended or adjusted under 35 U.S.C. 154(b) by 441 days.

(21) Appl. No.: 15/494,748

(22) Filed: Apr. 24, 2017

(65) Prior Publication Data

US 2017/0238857 A1   Aug. 24, 2017

Related U.S. Application Data

(63) Continuation of application No. 15/388,994, filed on Dec. 22, 2016, now abandoned.
(Continued)

(51) Int. Cl.
| | | |
|---|---|---|
| *A61B 5/15* | (2006.01) | |
| *B01L 3/00* | (2006.01) | |
| *A61B 5/151* | (2006.01) | |

(52) U.S. Cl.
CPC ........ *A61B 5/150343* (2013.01); *A61B 5/151* (2013.01); *A61B 5/150022* (2013.01);
(Continued)

(58) Field of Classification Search
CPC ........ A61B 5/150343; A61B 5/150022; A61B 5/150267; A61B 5/150755; A61B 5/151;
(Continued)

(56) References Cited

U.S. PATENT DOCUMENTS

| | | | |
|---|---|---|---|
| 4,576,185 A | * | 3/1986 | Proud .................. B01L 3/5082 600/573 |
| 5,725,831 A | | 3/1998 | Reichler et al. |

(Continued)

FOREIGN PATENT DOCUMENTS

| | | |
|---|---|---|
| CN | 101754812 B | 6/2013 |
| CN | 104107058 A | 10/2014 |

(Continued)

OTHER PUBLICATIONS

Schaff et al. "Vascular mimetics based on microfluidics for imaging the leukocyte-endothelial inflammatory response" Lab Chip, 2007, 7, 448-456 (Year: 2007).*

(Continued)

*Primary Examiner* — Samuel P Siefke
*Assistant Examiner* — Quocan B Vo
(74) *Attorney, Agent, or Firm* — Wolf, Greenfield & Sacks, P.C.

(57) ABSTRACT

Articles and methods for collecting and/or facilitating transfer of fluids are generally provided. In some embodiments, an article comprises a fluid collection region for introducing a fluid, such as a sample (e.g., blood sample) or a reagent, into a fluidic system. The articles and methods described herein may be useful for facilitating the filling of relatively small channels with a fluid, such as channels of a microfluidic device. The articles and methods may, for example, interface with a patient sample (e.g., a droplet of blood), or with a macroscopic fluid source such as a pipette or syringe. In certain embodiments, articles and methods described herein may increase the ease of collecting a fluidic sample from a patient, prevent or reduce spillage of the fluidic sample, reduce contamination of a fluidic sample, and/or prevent or reduce air from entering a fluidic sample or device compared to certain existing fluid collection devices.

20 Claims, 20 Drawing Sheets

Related U.S. Application Data

(60) Provisional application No. 62/272,173, filed on Dec. 29, 2015.

(52) U.S. Cl.
CPC .. *A61B 5/150267* (2013.01); *A61B 5/150358* (2013.01); *A61B 5/150755* (2013.01); *B01L 3/502715* (2013.01); *B01L 2200/027* (2013.01); *B01L 2400/0406* (2013.01)

(58) Field of Classification Search
CPC ......... B01L 3/502715; B01L 2200/027; B01L 2400/0406
See application file for complete search history.

(56) References Cited

U.S. PATENT DOCUMENTS

| | | |
|---|---|---|
| 6,818,185 B1 | 11/2004 | Petersen et al. |
| D645,971 S | 9/2011 | Taylor et al. |
| 8,202,492 B2 | 6/2012 | Linder et al. |
| 8,221,700 B2 | 7/2012 | Steinmiller et al. |
| 8,222,049 B2 | 7/2012 | Linder et al. |
| 8,409,527 B2 | 4/2013 | Linder et al. |
| 8,475,737 B2 | 7/2013 | Linder et al. |
| 8,480,975 B2 | 7/2013 | Steinmiller et al. |
| 8,567,425 B2 | 10/2013 | Tan et al. |
| 8,580,569 B2 | 11/2013 | Linder et al. |
| 8,591,829 B2 | 11/2013 | Taylor et al. |
| 8,765,062 B2 | 7/2014 | Linder et al. |
| 8,802,029 B2 | 8/2014 | Steinmiller et al. |
| 8,802,445 B2 | 8/2014 | Linder et al. |
| 8,915,259 B2 | 12/2014 | Tan et al. |
| 8,932,523 B2 | 1/2015 | Linder et al. |
| 9,075,047 B2 | 7/2015 | Linder et al. |
| 9,075,051 B2 | 7/2015 | Tan et al. |
| 9,116,124 B2 | 8/2015 | Linder et al. |
| 9,181,292 B2 | 11/2015 | Liang |
| 9,234,888 B2 | 1/2016 | Linder et al. |
| 9,255,866 B2 | 2/2016 | Dirckx et al. |
| 9,555,408 B2 | 1/2017 | Tan et al. |
| 9,561,506 B2 | 2/2017 | Taylor et al. |
| 9,588,027 B2 | 3/2017 | Dirckx et al. |
| 9,592,505 B2 | 3/2017 | Linder et al. |
| 2002/0155033 A1* | 10/2002 | Strand .............. B01J 19/0093 422/400 |
| 2004/0141880 A1 | 7/2004 | Handler et al. |
| 2005/0229722 A1* | 10/2005 | Howell ............ A61B 5/150343 73/864.72 |
| 2008/0312576 A1 | 12/2008 | McKinnon et al. |
| 2009/0075390 A1 | 3/2009 | Linder et al. |
| 2009/0291507 A1* | 11/2009 | Clemmens ........ B01L 3/502738 436/501 |
| 2011/0212002 A1* | 9/2011 | Curry .................. B01L 3/5029 422/430 |
| 2012/0231488 A1* | 9/2012 | Marshall .......... B01L 3/502715 435/29 |
| 2013/0114075 A1 | 5/2013 | Hukari et al. |
| 2013/0273643 A1 | 10/2013 | Vickers et al. |
| 2013/0343955 A1* | 12/2013 | Doyle ................. B01L 3/5055 422/82.02 |
| 2014/0234180 A1 | 8/2014 | Linder et al. |
| 2014/0309555 A1 | 10/2014 | Gelfand et al. |
| 2015/0086997 A1 | 3/2015 | Linder et al. |
| 2015/0196908 A9 | 7/2015 | Steinmiller et al. |
| 2015/0251178 A1 | 9/2015 | Tan et al. |
| 2015/0322272 A1* | 11/2015 | Pokroy .................. B05D 1/60 428/141 |
| 2015/0343443 A1 | 12/2015 | Linder et al. |
| 2016/0025732 A1 | 1/2016 | Linder et al. |
| 2016/0077087 A1 | 3/2016 | Linder et al. |
| 2016/0207042 A1 | 7/2016 | Dirckx et al. |
| 2016/0229881 A1 | 8/2016 | Liang |
| 2016/0282349 A1 | 9/2016 | Linder et al. |
| 2016/0305878 A1 | 10/2016 | Steinmiller et al. |
| 2016/0305937 A1 | 10/2016 | Steinmiller et al. |
| 2016/0305938 A1 | 10/2016 | Linder et al. |
| 2016/0320394 A1 | 11/2016 | Dong et al. |

FOREIGN PATENT DOCUMENTS

| | | |
|---|---|---|
| CN | 204705517 U | 10/2015 |
| CN | 106456439 A | 2/2017 |
| CN | 106999120 A | 8/2017 |
| DE | 102013012237 A1 | 1/2015 |
| WO | WO 00/76663 A1 | 12/2000 |
| WO | WO 2005/066613 A1 | 7/2005 |
| WO | WO 2005/072858 A1 | 8/2005 |
| WO | WO 2006/113727 A2 | 10/2006 |
| WO | WO 2013/102201 A1 | 7/2013 |

OTHER PUBLICATIONS

Berthier et al. "A generalization of the Lucas-Washburn-Rideal law to composite microchannels of arbitrary cross section" May 24, 2015, Microfluid Nanofluid (2015) 19:497-507, hereinafter Berthier (Year: 2015).*

Golas et al. "Surface-Energy Dependent Contact Activation of Blood Factor XII" Biomaterials. Feb. 2010; 31(6): 1068, hereinafter Golas (Year: 2010).*

Cho et al. "How the capillary burst microvalve works" Nov. 3, 2006, Journal of Colloid and Interface Science 306 379-385, hereinafter Cho (Year: 2006).*

International Search Report and Written Opinion for PCT/US2016/068288 dated Apr. 11, 2017.

Extended European Search Report for EP App. No. 16882422.5 dated Jul. 8, 2019.

EP 16882422.5, Jul. 8, 2019, Extended European Search report.

* cited by examiner

500

FLUID COLLECTION DEVICE AND RELATED METHODS

RELATED APPLICATIONS

The present application is a continuation of U.S. patent application Ser. No. 15/388,994, filed Dec. 22, 2016, which claims priority to U.S. Provisional Application No. 62/272,173, filed Dec. 29, 2015, each of which is hereby incorporated by reference in its entirety for all purposes.

TECHNICAL FIELD

The present invention generally relates to articles and methods for collecting and/or facilitating transfer of fluids.

SUMMARY

The present invention generally relates to articles and methods for collecting and/or facilitating transfer of fluids, such as fluidic samples and reagents.

In one aspect, articles for introducing a fluid into a fluidic system are provided. In some embodiments, the article comprises a fluid collection region comprising a substantially vertical edge having a thickness of less than or equal to 2 mm, a sidewall, and a bottom portion, wherein the fluid collection region has a holding volume of less than or equal to about 200 microliters and a longest dimension of less than about 2 cm, and a channel integrally connected to and in fluidic communication with the fluid collection region, wherein the channel has an average cross sectional dimension of at least 0.1 mm and less than or equal to about 5 mm, and a length of at least about 1 mm and less than or equal to about 10 mm.

In some embodiments, the article comprises a fluid collection region comprising an edge, a sidewall, and a bottom portion, and a receiving channel integrally connected to and in fluidic communication with the fluid collection region, wherein the receiving channel includes a concave portion adapted and arranged to receive a fluidic channel.

In some embodiments, the article comprises a fluid collection region comprising a curved edge, a sidewall, and a bottom portion, a channel integrally connected to and in fluidic communication with the fluid collection region, wherein the receiving channel is adapted and arranged to be in fluidic communication with a fluidic channel comprising a fluid path having a fluid path inlet and a fluid path outlet, and wherein the fluid collection region is adapted and arranged to hold a control fluid having a critical volume of less than or equal to about 20 microliters without filling the fluidic channel, and to allow flow of the control fluid into the fluidic channel when the volume of the control fluid is at least about 25 microliters, and wherein the control fluid is deionized water. In other embodiments, the control fluid is another control fluid described herein.

In some embodiments, the device comprises a fluidic connector comprising a fluidic channel that includes a fluid path having a fluid path inlet and a fluid path outlet, wherein the fluidic connector is adapted and arranged to connect to an inlet and/or an outlet of a fluidic device, and a fluid collection device for introducing a fluid into the fluidic connector, the fluid collection device comprising a fluid collection region comprising an edge, a sidewall, a bottom portion, and a receiving channel integrally connected to and in fluidic communication with the fluid collection region.

In another aspect, devices are provided. In some embodiments, the device comprises a fluidic system comprising at least one channel having an inlet and an outlet, a fluidic connector comprising a fluidic channel that includes a fluid path having a fluid path inlet and a fluid path outlet, wherein the fluidic connector is adapted and arranged to fasten with the fluidic system and allow fluid communication between the fluidic system and the fluidic connector, and a fluid collection device for introducing a fluid into the fluidic connector, the fluid collection device comprising a fluid collection region and a channel that is adapted and arranged to reversibly connect with the fluidic channel of the fluidic connector.

In yet another aspect, methods are provided. In some embodiments, the method comprises contacting a droplet of blood positioned on a surface with a fluid collection device comprising a fluid collection region comprising an edge and a sidewall and a channel integrally connected to and in fluidic communication with the fluid collection region, scraping the surface with the edge of the fluid collection region, and introducing at least a portion of the droplet into the fluid collection region.

In some embodiments, the method comprises contacting a fluid with a fluid collection device comprising a fluid collection region comprising an edge, a sidewall and a bottom portion, and a channel integrally connected to and in fluidic communication with the fluid collection region, wherein the fluid collection device has a holding volume of less than or equal to 5 mL, allowing the fluid to flow against the sidewall of the fluid collection region by gravity, and transferring at least a portion of the fluid from the fluid collection device to a fluidic channel that is reversibly connected to the fluid collection device.

Other advantages and novel features of the present invention will become apparent from the following detailed description of various non-limiting embodiments of the invention when considered in conjunction with the accompanying figures. In cases where the present specification and a document incorporated by reference include conflicting and/or inconsistent disclosure, the present specification shall control.

BRIEF DESCRIPTION OF THE DRAWINGS

Non-limiting embodiments of the present invention will be described by way of example with reference to the accompanying figures, which are schematic and are not intended to be drawn to scale. In the figures, each identical or nearly identical component illustrated is typically represented by a single numeral. For purposes of clarity, not every component is labeled in every figure, nor is every component of each embodiment of the invention shown where illustration is not necessary to allow those of ordinary skill in the art to understand the invention. In the figures.

DETAILED DESCRIPTION

Articles and methods for collecting and/or facilitating transfer of fluids are generally provided. In some embodiments, an article comprises a fluid collection region for introducing a fluid, such as a sample (e.g., blood sample) or a reagent, into a fluidic system. The articles and methods described herein may be useful for facilitating the filling of relatively small channels with a fluid, such as channels of a microfluidic device. The articles and methods may, for example, interface with a patient sample (e.g., a droplet of blood), or with a macroscopic fluid source such as a pipette or syringe. In certain embodiments, articles and methods described herein may increase the ease of collecting a fluidic sample from a patient, prevent or reduce spillage of the fluidic sample, reduce contamination of a fluidic sample, and/or prevent or reduce air from entering a fluidic sample or device compared to certain existing fluid collection devices.

Figure 1A:
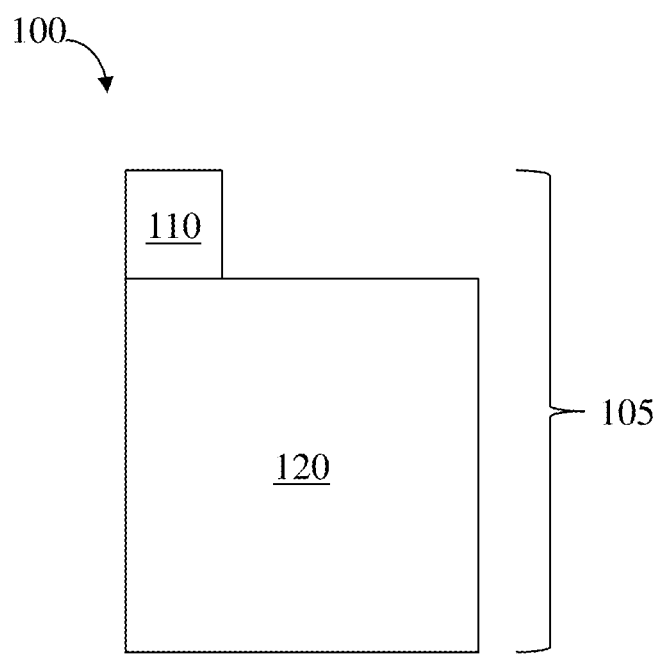
FIG. 1A is a schematic drawing of a fluid collection device, according to one set of embodiments.

In some embodiments, an article for collecting and/or facilitating transfer of fluids as described herein is a fluid collection device. The fluid collection device may comprise a fluid collection region comprising an edge and a sidewall. For example, as shown illustratively in FIG. 1A, a fluid collection device 100 comprises a fluid collection region 105 comprising an edge 110 and a sidewall 120. In some embodiments, edge 110 and sidewall 120 are in direct contact with each other (although not necessarily so). In some cases, the edge and the sidewall may be formed from a single material (e.g., molded). In other embodiments, the edge and the sidewall may be formed separately and joined together such that they are in direct contact with each other (e.g., via an adhesive or the like).

Figure 1B:
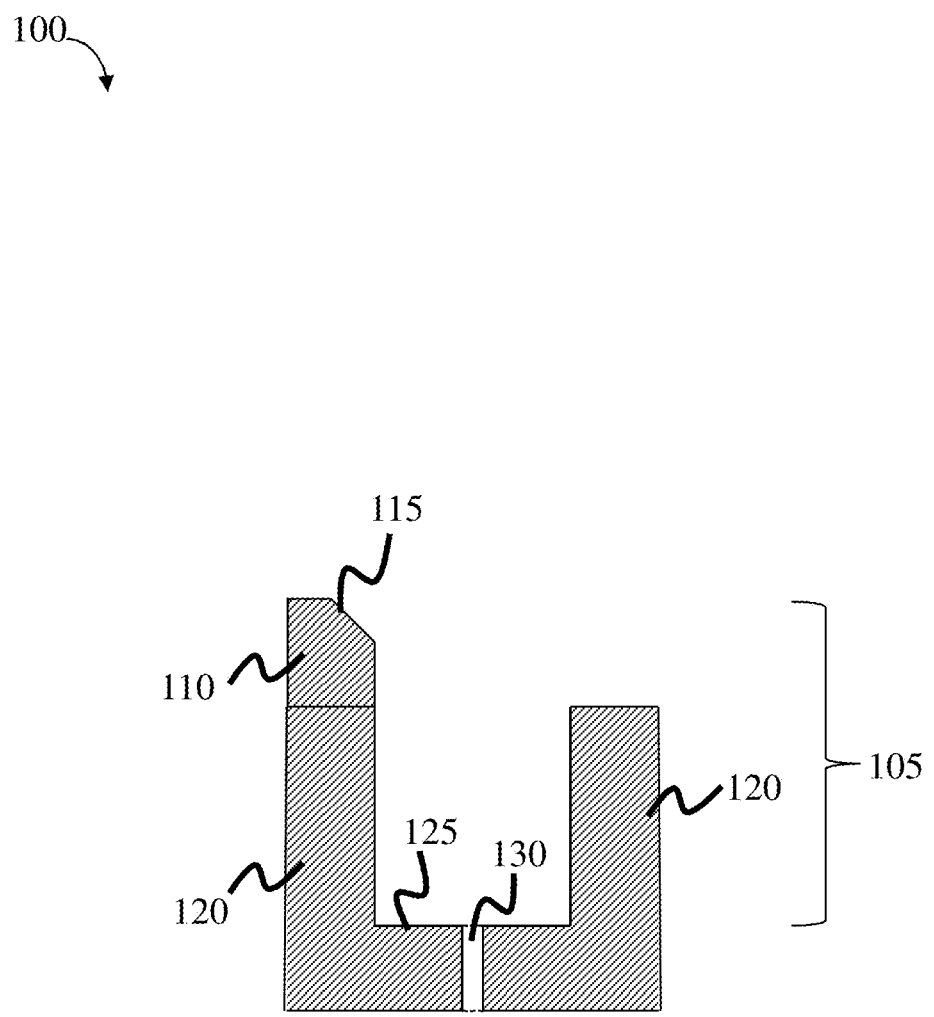
FIGS. 1B-1C are cross-sectional schematic drawings of a fluid collection device, according to one set of embodiments.

In some embodiments, at least a portion (e.g., a bottom portion) of the sidewall is configured and arranged to receive and/or hold a fluid. As shown illustratively in FIG. 1B, fluid collection device 100 (as shown as a cross-section of the fluid collection device) comprises fluid collection region 105. Fluid collection region 105 may encompass edge 110 and sidewall 120, where sidewall 120 includes or is attached to a bottom portion 125. In certain embodiments, the bottom portion is configured and arranged to receive and/or hold a fluid such as a fluid sample or reagent (e.g., blood). At least a portion of the edge, in some embodiments, may be tapered, as described in more detail below. For example, as shown in FIG. 1B, edge 110 may comprise tapered surface 115.

In certain embodiments, the fluid collection device includes a channel. The channel may facilitate transfer of fluid from the fluid collection device to another channel, device, or fluid container (e.g., a fluidic connector, as described in more detail below). In some embodiments, the channel is integrally connected to and in fluidic communication with the fluid collection region. For example, referring again to FIG. 1B, channel 130 may be integrally connected to and in fluidic communication with fluid collection region 105 (e.g., a bottom or side portion of the fluid collection region).

Figure 1C:
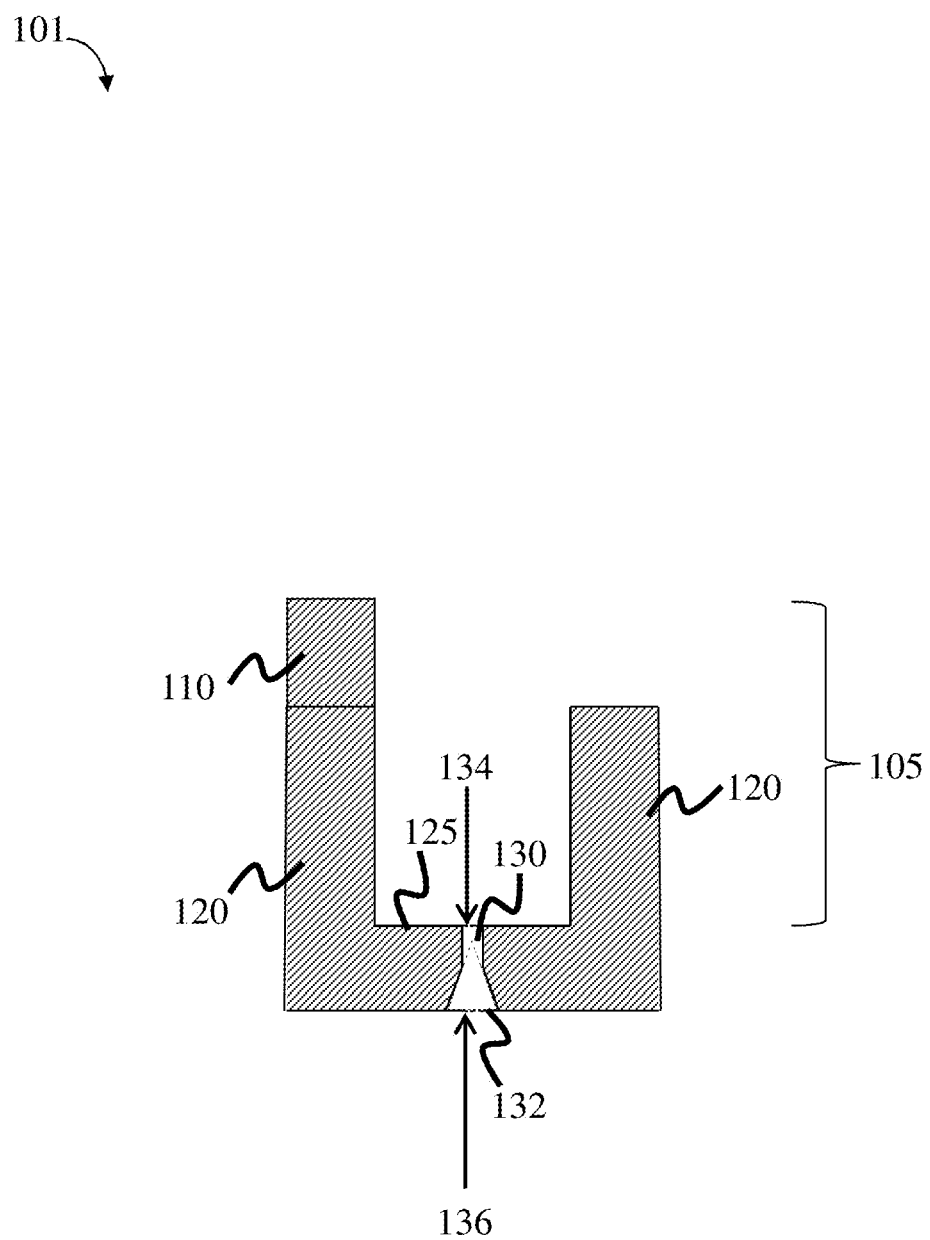

The channel connected to the fluid collection region may have any suitable shape and/or configuration. In some embodiments, at least a portion of the channel may be concave. For example, as shown illustratively in FIG. 1C, fluid collection device 101 comprises fluid collection region 105 including edge 110, sidewall 120, and channel 130. In some such embodiments, channel 130 may comprise concave portion 132. Concave portions of the channel may be used, for example, for guiding the insertion of a secondary channel, such as a fluidic channel and/or fluidic connector, into the channel of the fluid collection device. In some embodiments, the fluid collection device (and/or channel within the fluid collection device) may be configured such that a secondary channel is reversibly connected with at least a portion of the channel of the fluid collection device (or with the concave portion of the channel). Irreversible connections are also possible in some embodiments. In embodiments in which a secondary channel is inserted into a channel of the fluid collection device, the channel of the fluid collection device may be considered a receiving channel.

In other embodiments, a channel of a fluid collection device may include a convex portion, or a portion that extends outwards from the fluid collection device. Such a channel may, for example, be inserted into a secondary channel (e.g., a receiving channel of a fluid connector or device). Other configurations of channels on the fluid collection device are also possible.

In some embodiments, methods for collection a patient sample are provided. Some assays/devices require certain amounts of a patient sample (e.g., blood) to run the test. To obtain, for example, 12.4 microliters of blood in the device, one needs more than 15 microliters of blood on the finger. It is difficult to hold, for example, a 15-25 or 20-25 microliter droplet on a finger when the blood droplet is on top of the finger. The blood is very likely to slide off the finger in such amounts, and as a result, the patient tends to express as little blood as possible on the finger to avoid the droplet from sliding off. With a small droplet of blood, the user may scrape the blood with the end of the capillary to obtain any blood left on the finger to get all of the 12.4 microliters necessary for the device. In some instances, some of that blood might be already coagulating. During this process, however, any contaminants on the skin may be picked up in the sample. This process can therefore result in inaccurate results in some instances. For example, studies were performed which showed positive correlation between collection from a small blood droplet and failure of the test to complete normally (e.g., due to occurrence of a clog during flow of whole blood through the detection zones of a device).

The methods described herein may address these issues by allowing the patient to collect a larger and/or a less contaminated sample than otherwise would have been possible without such methods. For instance, in some embodiments, a device or a component of a device is filled (or the sample is introduced into the device) only after a critical volume of sample is obtained necessary for conducting an assay/use of the device. For example, a method may comprise introducing a certain volume of fluid (e.g., at least about 24 microliters or any other suitable volume described herein) into the fluid collection region of a device described herein, and transferring at least a portion (and in some embodiments, not all) of the fluid from the fluid collection device to a fluidic channel in fluid communication with and reversibly connected to the fluid collection device.

As described herein, in some embodiments, the fluid collection device may be used for collecting a fluid sample. During the step of collecting a fluid, at least a portion of the fluid collection device (e.g., at least a portion of the edge and/or tapered edge) may contact a surface and/or a fluid (e.g., a droplet) positioned on the surface. In certain embodiments, the surface comprises at least a portion of a surface of human skin of a patient (e.g., a blood droplet positioned on human skin, such as the skin of a finger or an ear lobe). In some embodiments, the surface of human skin is pierced (e.g., via a lancet, a needle, etc.) such that a droplet of blood is released. The edge of the fluid collection region may contact (e.g., scrape) the surface of the skin such that the droplet of blood is introduced into the interior of the fluid collection region. In an exemplary embodiment, the surface of the skin that has been pierced may include a droplet of blood thereon. The droplet of blood may be inverted (e.g., such that the droplet of blood hangs from the surface of the skin) and the blood can be collected by the fluid collection device by allowing the blood to flow against the sidewall of the fluid collection region (e.g., by contacting the sidewall to the blood such that the blood flows by gravity into the fluid collection device).

In some embodiments, a method comprises performing a finger stick (e.g., to form a droplet of blood on a surface of the finger); holding the finger such that the site of finger stick points downwards (e.g., such that the droplet of blood hangs from the surface of the skin); and using a collection device (as described herein) to collect single droplet of blood having a volume of greater than or equal to 12 microliters, greater than or equal to 13 microliters, greater than or equal to 14 microliters, greater than or equal to 15 microliters, greater than or equal to 16 microliters, greater than or equal to 17 microliters, greater than or equal to 18 microliters, greater than or equal to 19 microliters, greater than or equal to 20 microliters, greater than or equal to 21 microliters, greater than or equal to 22 microliters, greater than or equal to 23 microliters, greater than or equal to 24 microliters, greater than or equal to 25 microliters, greater than or equal to 26 microliters, greater than or equal to 27 microliters, greater than or equal to 28 microliters, greater than or equal to 29 microliters, or greater than or equal to 30 microliters. In some embodiments, the volume of the droplet is less than or equal to 35 microliters, less than or equal to 30 microliters, less than or equal to 25 microliters, less than or equal to 20 microliters, or less than or equal to 15 microliters. Combinations of the above referenced ranges are also possible (e.g., greater than or equal to 15 microliters and less than or equal to 35 mL). Other ranges are also possible. In some embodiments, instructions (e.g., written instructions) are provided to the user to perform the acts described above.

Figure 1D:
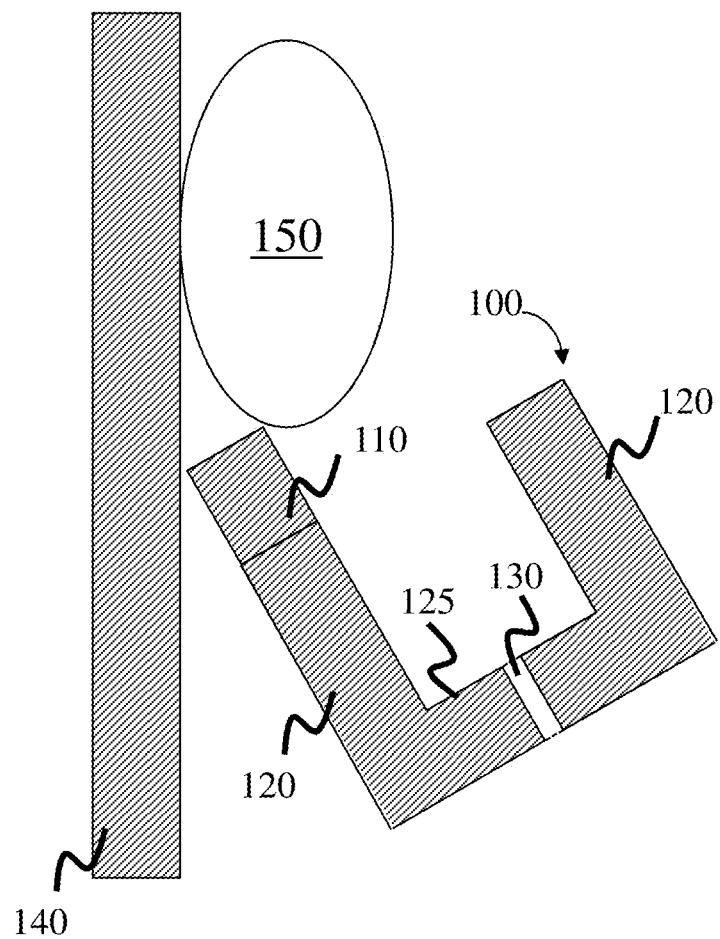
FIGS. 1D-1G are cross-sectional schematic drawings showing a method of collecting a fluid sample with a fluid collection device, according to one set of embodiments.

As one example, and as shown illustratively in FIG. 1D, edge 110 of fluid collection device 100 may contact a surface 140 and/or a fluid 150 (e.g., a droplet) positioned on the surface. In some embodiments, the edge is scraped along the surface. In some such embodiments, scraping the surface involves contacting the surface with the fluid collection device and moving the fluid collection device such that at least a portion of a fluid present on the surface is introduced into the fluid collection region. In some embodiments, at least a portion of the fluid, after contacting and/or scraping, flows along the sidewall (e.g., interior surface of sidewall 120 in FIG. 1D) of the fluid collection device. Fluid may flow against the sidewall of the fluid collection region by gravity, e.g., by rotating the fluid collection device such that the fluid flows into a bottom portion 125 of the fluid collection device. In some cases, the sidewall may be coated (e.g., with a hydrophilic coating) to facilitate fluid flow against the sidewall. In certain embodiments, at least a portion of the fluid contacts a channel of the fluid collection device (e.g., channel 130 in FIG. 1D). At least a portion of the fluid may enter the channel (e.g., a receiving channel).

Figure 1E:
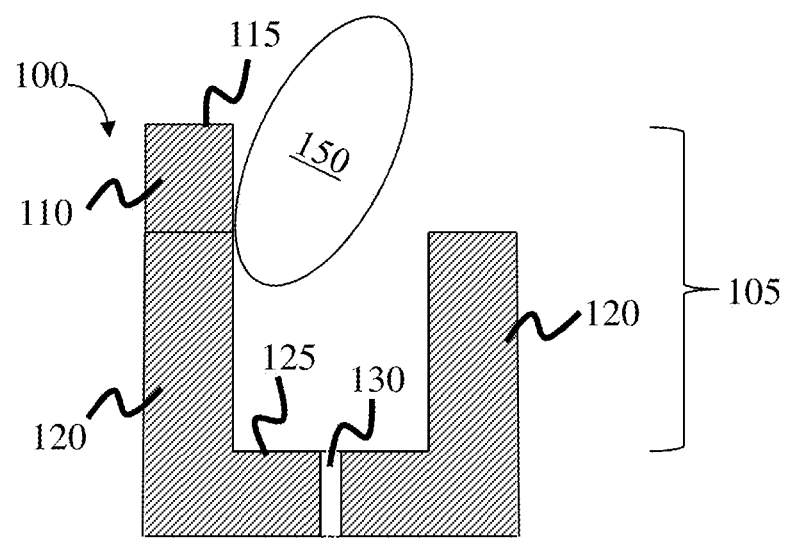

In certain embodiments, a fluid may be introduced (e.g., dispensed) into the fluid collection region without scraping. For example, as shown illustratively in FIG. 1E, fluid 150 may be introduced into fluid collection region 105 of fluid collection device 100 directly. The fluid may be introduced into the fluid collection using any suitable method including, but not limited to, dripping, dispensing (e.g., dispensed via a pipette, dispensed via a syringe, dispensed via a capillary tube), pouring, condensing, and spraying. In some embodiments, the fluid is introduced onto a surface of the sidewall.

In some embodiments, the fluid collection region is adapted and arranged such that it holds a fluid of particular volume (or range of volumes) before the fluid beings to fill a channel of the fluid collection device (or a fluid path inserted into the channel, such as a capillary tube). For instance, in some embodiments, the fluid collection region may hold a particular volume of fluid without the fluid filling the channel (or fluid path, such as a fluid path inlet) in fluidic communication with the fluid collection region (e.g., a channel at the bottom or side of the fluid collection region). In some such embodiments, the fluid may only enter the channel (or a fluid path within the channel) upon the fluid reaching a volume greater than a particular critical volume. The fluid may enter the channel (or fluid path inserted in the channel) by gravity and without any applied (positive or negative pressure) applied to the channel or fluid collection region. Advantageously, holding the fluid until a particular volume is present within the fluid collection region may, for example, prevent the formation of air bubbles in the channel (or fluid path) during collecting of the fluid. For example, during collection of a sample (e.g., collection of blood from a surface of finger as a result of a finger prick), if the sample is collected in 5 microliter increments for a total of 30 microliters, and assuming the critical volume required to initiate flow into the channel is 26 microliters, the sample would not flow into the channel (or fluid path) until 30 microliters is present in the fluid collection region. By contrast, if the geometry of the fluid collection region did not allow for fluid to accumulate until a critical volume had been reached before flow was initiated, each 5 microliter sample would fill the channel (or fluid path inserted in the channel) upon entering the fluid collection region. In this scenario, air bubbles may be present between each 5 microliter volume in the channel.

The critical volume of a particular fluid collection device, i.e., the volume of fluid that the fluid collection region can hold prior to filing of a channel (or a fluid path within/inserted in the channel) connected to the fluid collection region, may be determined by collecting a control fluid (e.g., deionized water, an aqueous dye solution, or a reference material such as total prostate specific antigen (TPSA) External Control Matrix) in the fluid collection region and measuring the minimum volume required for the fluid to fill a channel (or a fluid path within the channel) connected to and in fluidic communication with the fluid collection region. For example, referring to FIG. 1H, the critical volume of the fluid collection region may be determined by inserting a fluid path inlet 129 (e.g., a tube, such as a capillary tube, described in more detail below) into channel 130 (e.g., a receiving channel) and collecting fluid 150 (e.g., the control fluid) such that the fluid initially enters fluid collection region 105 and contacts bottom portion 125 (e.g., without the fluid initially touching channel 130) but does not fill the fluid path inlet, and then measuring the minimum volume of fluid 150 needed for the fluid path inlet to be filled.

In some embodiments, for purposes of determining the critical volume, the fluid is added in a manner such that it flows down at least a portion of the sidewall of the fluid collection region. Fluid path inlet 129 may be inserted in channel 130 (e.g., a receiving channel) such that a terminating end of the fluid path inlet is positioned (e.g., a maximum height or distance 131 of the fluid path extending from the bottom portion 125 of the fluid collection region may be) at least 50 microns, at least 100 microns, at least 150 microns, at least 200 microns, at least 250 microns, at least 290 microns, at least 300 microns, at least 400 microns, at least 500 microns, at least 1 mm, at least 2 mm, at least 3 mm, at least 4 mm, at least 5 mm, at least 6 mm, at least 7 mm, at least 8 mm, or at least 9 mm (e.g., above the opening to channel 130 at bottom portion 125); and/or less than or equal to 10 mm, less than or equal to 9 mm, less than or equal to 8 mm, less than or equal to 7 mm, less than or equal to 6 mm, less than or equal to 5 mm, less than or equal to 4 mm, than or equal to 3 mm, less than or equal to 2 mm, less than or equal to 1 mm, less than or equal to 500 microns, less than or equal to 400 microns, less than or equal to 300 microns, less than or equal to 290 microns, less than or equal to 200 microns, less than or equal to 100 microns, or less than or equal to 50 microns (e.g., above the opening to channel 130 at bottom portion 125) from the bottom portion of the fluid collection region. Combinations of the above-referenced ranges are also possible.

In some embodiments, the terminating end of the fluid path inlet may be positioned within the receiving channel and may not reach the bottom portion of the fluid collection region. For instance, the terminating end of the fluid path inlet may be positioned within the receiving channel at a distance from the bottom portion of the fluid collection region (e.g., the terminating end is positioned within channel 130) that is at least 50 microns, at least 100 microns, at least 150 microns, at least 200 microns, at least 250 microns, at least 290 microns, at least 300 microns, at least 400 microns, at least 500 microns, at least 1 mm, at least 2 mm, at least 3 mm, at least 4 mm, at least 5 mm, at least 6 mm, at least 7 mm, at least 8 mm, or at least 9 mm; and/or less than or equal to 10 mm, less than or equal to 9 mm, less than or equal to 8 mm, less than or equal to 7 mm, less than or equal to 6 mm, less than or equal to 5 mm, less than or equal to 4 mm, than or equal to 3 mm, less than or equal to 2 mm, less than or equal to 1 mm, less than or equal to 500 microns, less than or equal to 400 microns, less than or equal to 300 microns, less than or equal to 290 microns, less than or equal to 200 microns, less than or equal to 100 microns, or less than or equal to 50 microns. Combinations of the above-referenced ranges are also possible.

In certain embodiments, the ratio of the outer cross-sectional dimension of the fluid path inlet and the inner cross-sectional dimension of channel 130 (e.g., the receiving channel, which may be measured at opening 134) of the fluid collection device is between about 1:1.01 and about 1:1.25 or another suitable ratio as described herein. Those skilled in the art would understand that if the control fluid is added directly to the fluid path inlet, the control fluid could immediately fill the fluid path inlet, and the amount of control fluid added would not be considered the critical volume of the fluid collection device.

The fluid collection region may be designed to have any suitable critical volume. That is, the fluid collection region may be adapted and arranged to hold a control fluid having a particular volume without filling a channel connected to the fluid collection region (or a secondary channel disposed in the channel). In some embodiments, the critical holding volume of a control fluid may be less than or equal to 30 microliters, less than or equal to 25 microliters, less than or equal to 22 microliters, less than or equal to 20 microliters, less than or equal to 18 microliters, less than or equal to 16 microliters, less than or equal to 14 microliters, less than or equal to 12 microliters, less than or equal to 10 microliters, less than or equal to 5 microliters, less than or equal to 2 microliters, or less than or equal to 1 microliter. In certain embodiments, a critical holding volume of control fluid may be at least 0.1 microliters, at least 0.5 microliters, at least 1 microliter, at least 2 microliters, at least 5 microliters, at least 10 microliters, at least 12 microliters, at least 14 microliters, at least 16 microliters, or at least 18 microliters. Combinations of the above-referenced ranges are also possible (e.g., at least 0.1 microliters and less than or equal to 20 microliters). Other ranges are also possible. In some embodiments, the control fluid (e.g., having a volume of less than 20 microliters) may be introduced into the fluid collection region as described herein such that at least a portion of the control fluid contacts the channel (or a fluidic channel disposed therein) without filling the channel.

In some embodiments, the critical volume of a fluid collected using the fluid collection device may be less than or equal to 30 microliters, less than or equal to 25 microliters, less than or equal to 22 microliters, less than or equal to 20 microliters, less than or equal to 18 microliters, less than or equal to 16 microliters, less than or equal to 14 microliters, less than or equal to 12 microliters, less than or equal to 10 microliters, less than or equal to 5 microliters, less than or equal to 2 microliters, or less than or equal to 1 microliter. In certain embodiments, a critical holding volume of the fluid collected using the fluid collection device may be at least 0.1 microliters, at least 0.5 microliters, at least 1 microliter, at least 2 microliters, at least 5 microliters, at least 10 microliters, at least 12 microliters, at least 14 microliters, at least 16 microliters, or at least 18 microliters. Combinations of the above-referenced ranges are also possible (e.g., at least 0.1 microliters and less than or equal to 20 microliters).

In some embodiments, the control fluid is allowed to flow into and fill the channel (or a fluidic channel disposed therein, such a secondary channel described herein) when the volume of the control fluid is at least a volume greater than the critical volume of the fluid collection region. For example, for a fluid collection region having a critical volume of 20 microliters, a control fluid may be introduced into the fluid collection region such that at least a portion of the control fluid contacts the channel and does not fill the channel until the volume of the control fluid introduced is greater than 20 microliters. In the embodiments described herein, the control fluid used for determining the critical volume may be deionized water, an aqueous dye solution, or an external control as described herein. The critical volume was also evaluated with a blood sample (a non-controlled fluid).

In some embodiments, the fluid collection region of the fluid collection device has a particular total volume for containing or holding a fluid, i.e., a holding volume. The holding volume can be determined by adding increasing increments of fluid (at a temperature of 25° C. and under 1 atm of pressure) to the fluid collection region of the fluid collection device, held in a substantially vertical position relative to the sidewall, before at least a portion of the fluid reaches the top of the sidewalls of 120 or out through the channel 130. In such instances, the inlet and/or outlet of any channel in fluidic communication with the fluid collection region is closed. As such, the holding volume does not include any volume of fluid contained in any channel of the fluid collection device. Those skilled in the art would understand that the holding volume may include the volume of a meniscus that forms prior to the spilling of water out of the fluid collection region. Without wishing to be bound by theory, a meniscus may form as a result of fluid surface tension at the sidewall and/or at the bottom of the channel.

In certain embodiments, the fluid collection region may have a holding volume of less than or equal to 5 mL, less than or equal to 4 mL, less than or equal to 3 mL, less than or equal to 2 mL, less than or equal to 1 mL, less than or equal to 750 microliters, less than or equal to 500 microliters, less than or equal to 250 microliters, less than or equal to 200 microliters, less than or equal to 100 microliters, less than or equal to 50 microliters, less than or equal to 25 microliters, less than or equal to 12 microliters, less than or equal to 10 microliters, or less than or equal to 5 microliters. In some embodiments, the fluid collection region has a holding volume of greater than or equal to 1 microliter, greater than or equal to 5 microliters, greater than or equal to 10 microliters, greater than or equal to 12 microliters, greater than or equal to 25 microliters, greater than or equal to 50 microliters, greater than or equal to 100 microliters, greater than or equal to 200 microliters, greater than or equal to 250 microliters, greater than or equal to 500 microliters, greater than or equal to 500 microliters, greater than or equal to 750 microliters, greater than or equal to 1 mL, greater than or equal to 2 mL, greater than or equal to 3 mL, or greater than or equal to 4 mL. Combinations of the above referenced ranges are also possible (e.g., greater than or equal to 1 microliter and less than or equal to 5 mL, greater than or equal to 1 microliter and less than or equal to 200 microliters, greater than or equal to 12 microliters and less than or equal to 50 microliters). Other ranges are also possible.

Figure 1F:
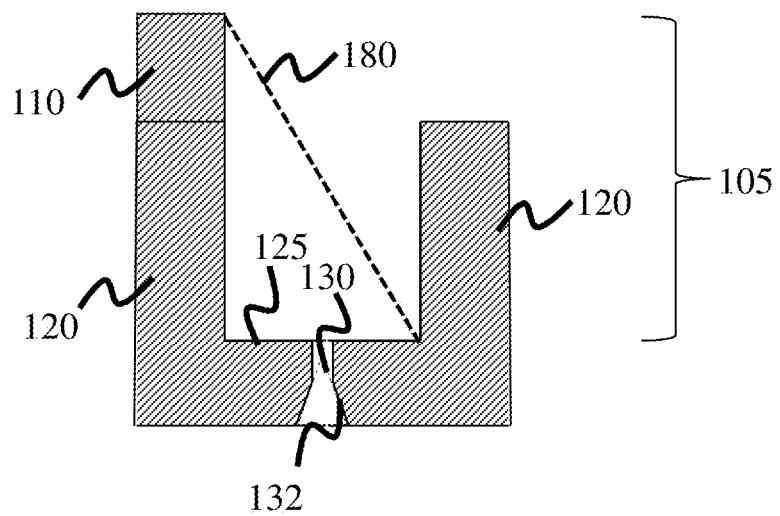

The fluid collection region may have any suitable dimensions. In some embodiments, the fluid collection region has a longest cross-sectional dimension within a particular range. The longest cross-sectional dimension of the fluid collection region, as described herein, is measured by determining the longest linear (e.g., straight-line) distance between two internal points on one or more of the edge (e.g., tapered edge), the bottom portion, and/or the sidewall of the fluid collection region (e.g., a sidewall integrally connected to and in fluidic communication with the fluid collection region). For example, as shown in FIG. 1F, in some embodiments, longest cross-sectional dimension 180 is measured by determining the linear distance between a furthermost internal point on the edge (e.g., edge 110 in FIG. 1F) from an internal point of the sidewall (e.g., sidewall 120 in FIG. 1E) of fluid collection device 101. In certain embodiments, the longest cross-sectional dimension is the furthest distance between two points on the bottom and/or the edge. For example, in some embodiments, bottom portion 125 is curved and the longest dimension of the fluid collection region may be measured by determining the linear distance between the furthermost internal point on the edge (e.g., edge 110 in FIG. 1F) and the bottom-most point of the bottom portion (e.g., bottom portion 125 in FIG. 1F).

In some embodiments, the longest cross-sectional dimension of the fluid collection region is less than or equal to 5 cm, less than or equal to 2 cm, less than or equal to 1.5 cm, less than or equal to 1 cm, less than or equal to 0.5 cm, less than or equal to 0.2 cm, or less than or equal to 0.1 cm. In certain embodiments, the longest cross-sectional dimension of the fluid collection region is greater than or equal to 0.05 cm, greater than or equal to 0.1 cm, greater than or equal to 0.2 cm, greater than or equal to 0.5 cm, greater than or equal to 1 cm, or greater than or equal to 1.5 cm. Combinations of the above-referenced ranges are also possible (e.g., greater than or equal to 0.05 cm and less than or equal to 2 cm). As described herein, the fluid collection region may include an edge, i.e., an outermost portion of the fluid collection region. The edge may facilitate collection of a fluid, such as when the edge is scraped against a surface on which a droplet of fluid is positioned.

In some embodiments, the edge may have a particular shape. In certain embodiments, the edge may be rounded or curved. For example, as shown illustratively in FIGS. 2A-2C, a fluid collection device 200 comprises a fluid collection region 202. Fluid collection region 202 may comprise an edge 210, a sidewall 220, a bottom portion 225, and a channel 230. In some such embodiments, edge 210 may be curved and may have a particular radius of curvature. In certain embodiments, the radius of curvature of the edge may be greater than or equal to 1 mm, greater than or equal to 2 mm, greater than or equal to 3 mm, 5 mm, greater than or equal to 6 mm, greater than or equal to 7 mm, greater than or equal to 8 mm, or greater than or equal to 9 mm. In some embodiments, the radius of curvature of the edge is less than or equal to 10 mm, less than or equal to 9 mm, less than or equal to 8 mm, less than or equal to 7 mm, less than or equal to 6 mm, less than or equal to 5 mm, less than or equal to 3 mm, or less than or equal to 2 mm. Combinations of the above referenced ranges are also possible (e.g., greater than or equal to 1 mm and less than or equal to 10 mm, greater than or equal to 5 mm and less than or equal to 10 mm). Other ranges are also possible. In certain embodiments, the edge is substantially linear in shape. Other edge geometries and shapes are also possible, including but not limited to V-shaped, U-shaped, rectangular, polygonal with n sides (e.g., with a large n, the polygonal shape may approximate a circular shape), elliptical, and compound curves. The edge may have a shape substantially similar to the shape of the sidewall.

Figure 1G:
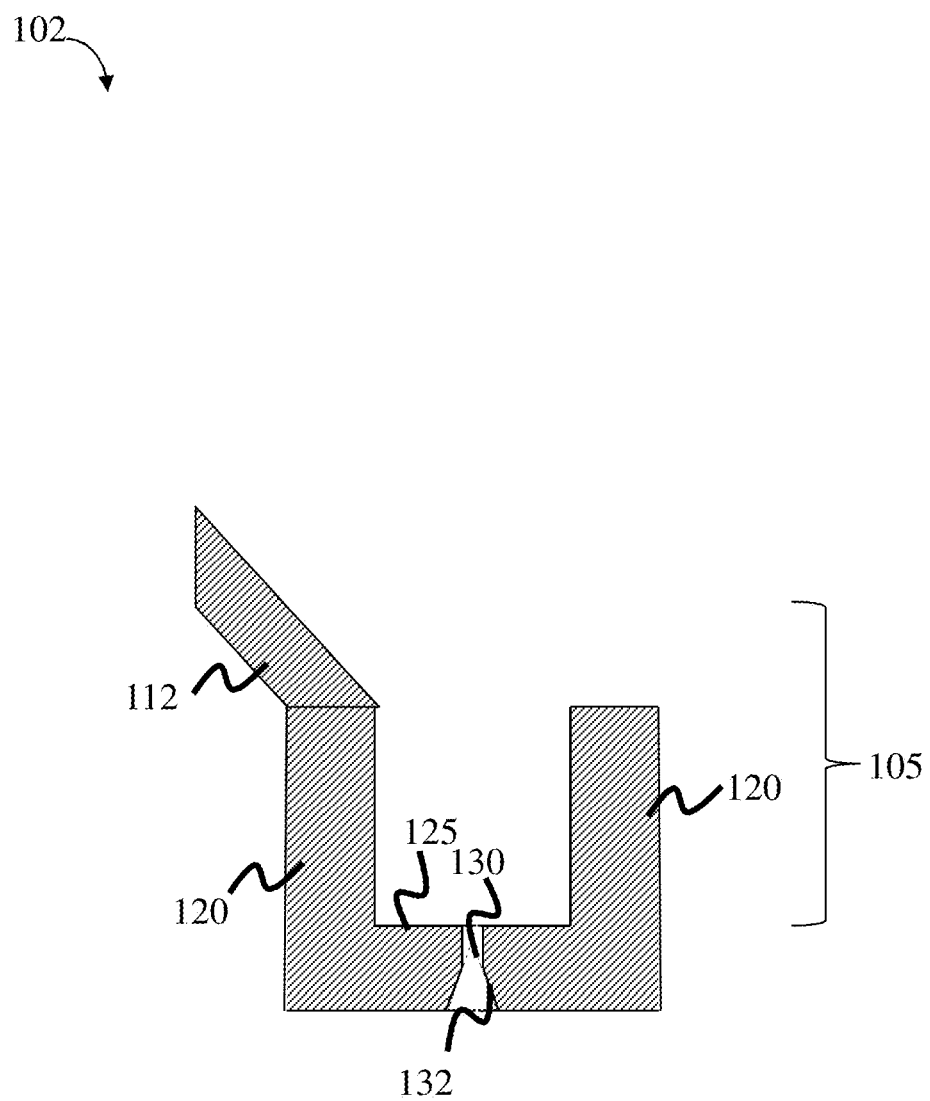
Figure 1H:
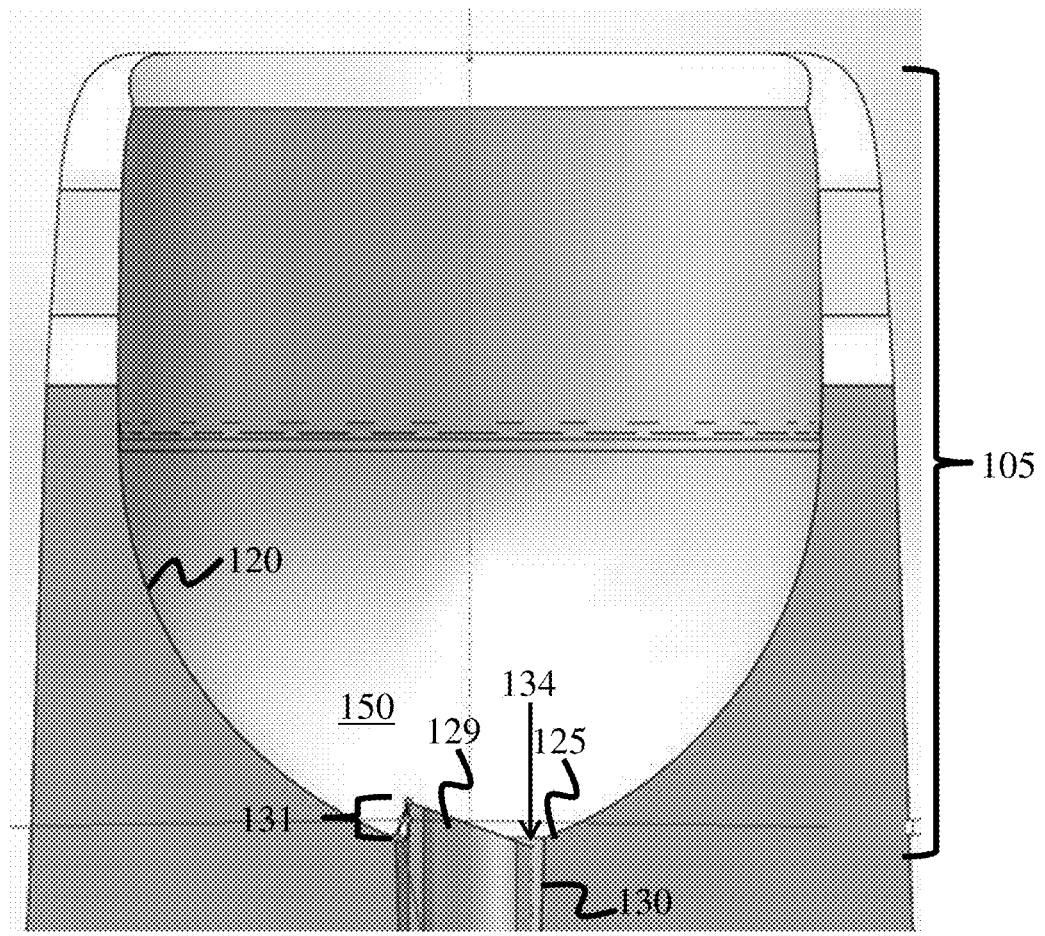
FIG. 1H is a cross-sectional schematic drawing of a fluid collection device, according to one set of embodiments.

In some embodiments, at least a portion of the edge is oriented within 45 degrees, within 40 degrees, within 35 degrees, within 30 degrees, within 25 degrees, within 20 degrees, within 15 degrees, within 10 degrees, within 5 degrees, within 2 degrees, or within 1 degree of vertical (relative to the orientation of a channel of the fluid collection device). Other angles are also possible. For example, as illustrated in FIG. 1G, fluid collection device 102 comprises edge 112 and a portion of the edge oriented within 45 degrees of vertical. In some embodiments, all or a portion of the edge is substantially vertical. In certain embodiments, all or a portion of the edge is within at least one of the angles noted above, relative to the orientation of a channel of the fluid collection device. For example, referring again to FIGS. 2A-2C, in some embodiments, fluid collection device 200 comprises edge 210 which is substantially vertical.

In certain embodiments, the edge is tapered. A tapering edge may facilitate the transfer of a fluid from a surface to the fluid collection region. In some cases, the tapered edge may reduce or prevent the presence of air bubbles in the collected fluid and/or prevent contamination of the collected fluid. As shown in FIG. 1B, tapered surface 115 may be located on an inner side relative to the fluid collection region. However, the tapered surface may be located on an outer side relative to the fluid collection region. In certain embodiments, both an inner side and an outer side of edge 110 may be tapered. Referring again to FIGS. 2A-2C, fluid collection region 202 may comprise a tapered edge 215 in direct contact with edge 210. In some embodiments, the tapered edge may have any suitable taper angle, as measured versus the orientation of a channel of the fluid collection device. In certain embodiments, the taper angle of the tapered edge is at least 0 degrees, at least 1 degree, at least 5 degrees, at least 10 degrees, at least 20 degrees, at least 30 degrees, at least 45 degrees, at least 60 degrees, at least 70 degrees, or at least 80 degrees. In some embodiments, the taper angle of the tapered edge may be less than or equal to 90 degrees, less than or equal to 80 degrees, less than or equal to 70 degrees, less than or equal to 60 degrees, less than or equal to 45 degrees, less than or equal to 30 degrees, less than or equal to 20 degrees, less than or equal to 10 degrees, less than or equal to 5 degrees, or less than or equal to 1 degree. Combinations of the above-referenced ranges are also possible (e.g., at least 1 degree and less than or equal to 90 degrees). Other ranges are also possible.

The edge of the fluid collection region may have any suitable maximum thickness. For example, in some embodiments, the maximum thickness of the edge is less than 2 mm, less than 1.5 mm, less than 1 mm, less than 0.5 mm, less than 0.25 mm, or less than or equal to 0.1 mm. In certain embodiments, the maximum thickness of the edge is greater than or equal to 0.05 mm, greater than or equal to 0.1 mm, greater than or equal to 0.25 mm, greater than or equal to 0.5 mm, greater than or equal to 1 mm, or greater than or equal to 1.5 mm. Combinations of the above-referenced ranges are possible (e.g., greater than or equal to 0.1 mm and less than 2 mm). Other ranges are also possible. In some embodiments, the edge may not have a uniform thickness.

As described herein, a fluid collection region may include a sidewall. The sidewall may facilitate the holding of a volume of fluid to be collected. In some embodiments, the sidewall may include one or more channels (e.g., for transferring a fluid) as described herein. The sidewall may, in some cases, allow for the collection of a particular volume of a fluid in the fluid collection region without filling the one or more channels until a minimum holding volume is exceeded within the fluid collection region, as described above. Advantageously, the sidewall may, in some embodiments, prevent spillage and/or contamination of a fluid to be collected prior to transfer of the fluid to a fluidic connector and/or fluidic system.

The sidewall may have any suitable shape. For example, in certain embodiments, the sidewall may have at least one cross-section, measured relative to vertical, which has a shape such as a square, rectangle, polygon, ellipse, circle, or triangle. For example, referring again to FIGS. 2A-2C, sidewall 220 comprises at least one cross-section, measured relative to vertical, which has a circular shape. Other shapes are also possible.

The sidewall of the fluid collection region may have any suitable maximum thickness. For example, in some embodiments, the maximum thickness of the sidewall is less than 5 mm, less than 3 mm, less than 2 mm, less than 1.5 mm, less than 1 mm, less than 0.5 mm, or less than 0.25 mm. In certain embodiments, the maximum thickness of the sidewall is greater than or equal to 0.1 mm, greater than or equal to 0.25 mm, greater than or equal to 0.5 mm, greater than or equal to 1 mm, or greater than or equal to 1.5 mm. Combinations of the above-referenced ranges are possible (e.g., greater than or equal to 0.1 mm and less than 2 mm). Other ranges are also possible. In some embodiments, the sidewall may have a varying thickness (e.g., across a length, width, or circumference of the sidewall).

In some embodiments, the sidewall (or fluid collection region formed by the sidewalls) has a particular largest cross-sectional dimension. The largest cross-sectional dimension may be a linear dimension measured from one portion of the sidewall to an opposing portion of the sidewall, e.g., dimension 231 shown in FIG. 2A. In some embodiments, the largest cross-sectional dimension may be a width or diameter of the fluid collection region formed by the sidewalls. In some embodiments, the largest cross-sectional dimension of the sidewall (or fluid collection region formed by the sidewalls) is less than or equal to 2 cm, less than or equal to 1.5 cm, less than or equal to 1 cm, less than or equal to 0.5 cm, less than or equal to 0.2 cm, less than or equal to 0.1 cm, less than or equal to 0.05 cm, or less than or equal to 0.02 cm. In certain embodiments, the largest cross-sectional dimension of the sidewall (or fluid collection region formed by the sidewalls) is greater than or equal to 0.01 cm, greater than or equal to 0.02 cm, greater than or equal to 0.05 cm, greater than or equal to 0.1 cm, greater than or equal to 0.2 cm, greater than or equal to 0.5 cm, greater than or equal to 1 cm, or greater than or equal to 1.5 cm. Combinations of the above-referenced ranges are also possible (e.g., greater than or equal to 0.01 cm and less than or equal to 2 cm).

Figure 2A:
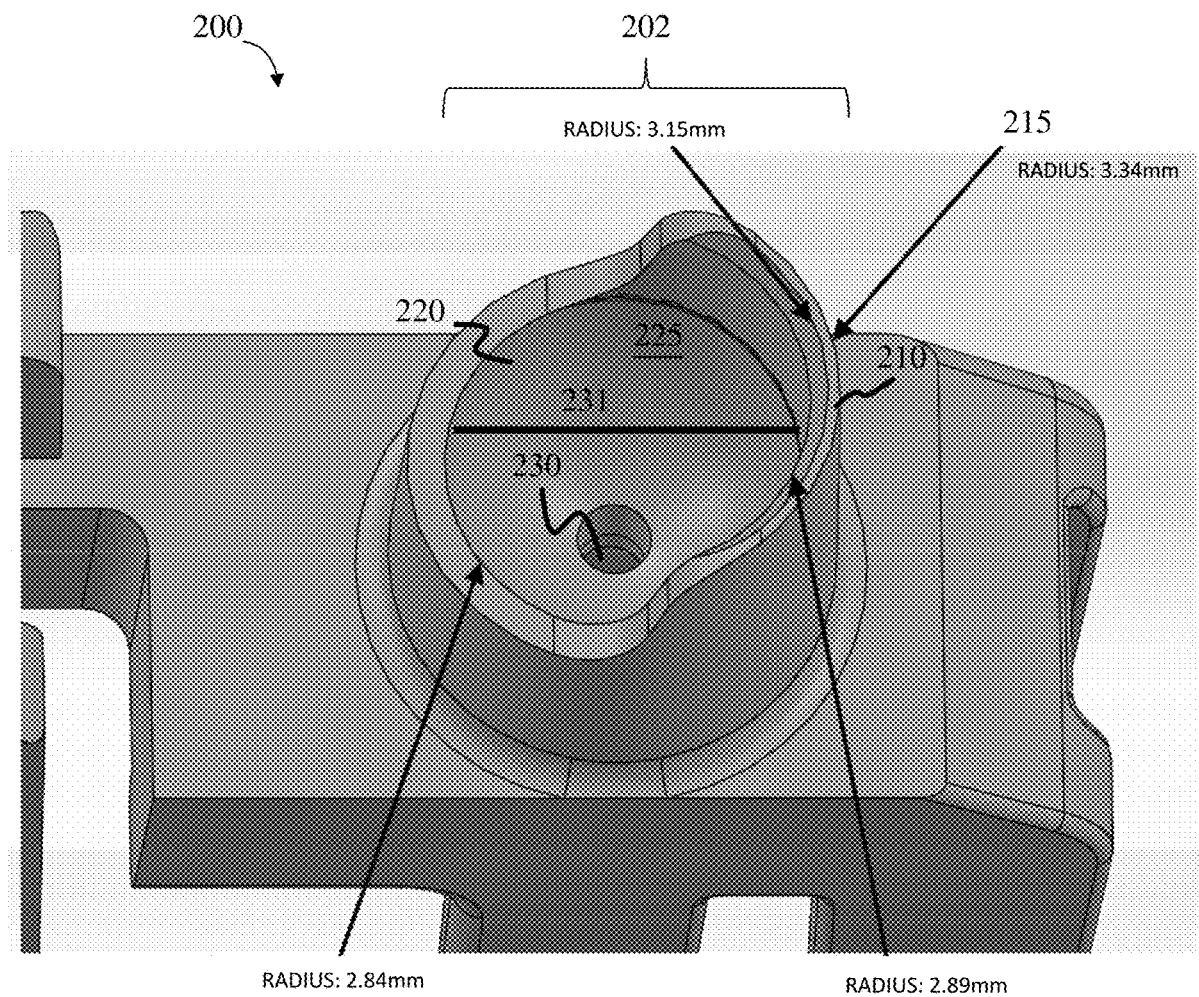
FIG. 2A is a top perspective view of a fluid collection region of a fluid collection device, according to one set of embodiments.
Figure 2B:
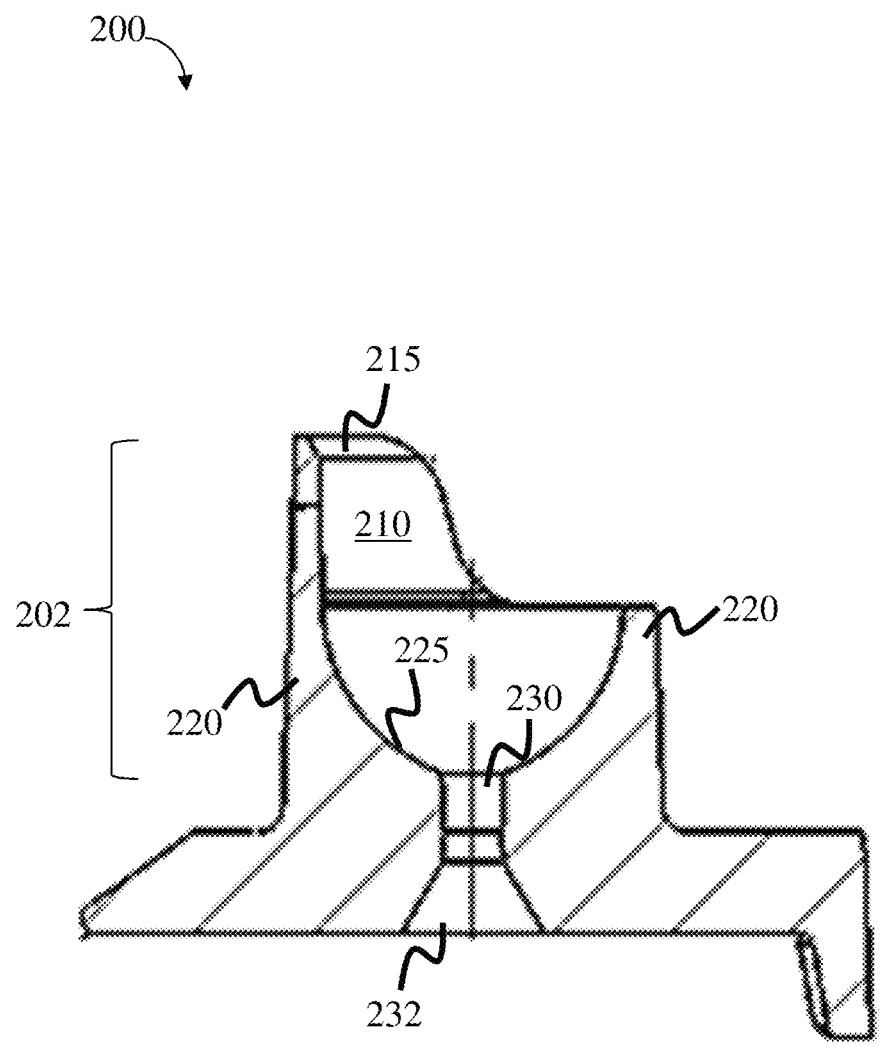
FIGS. 2B-2C are cross-sectional schematic drawings of a fluid collection device, according to one set of embodiments.
Figure 2C:
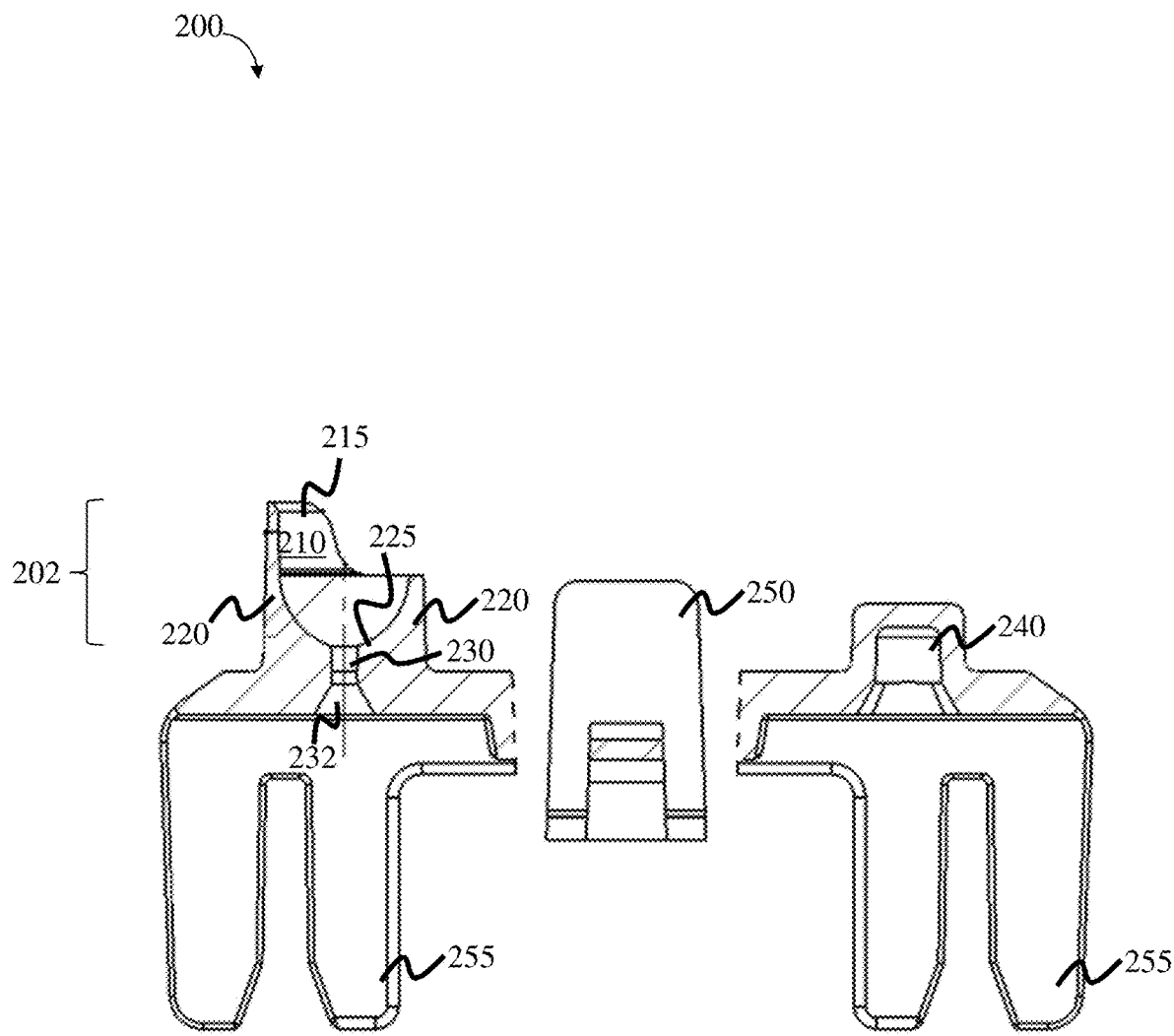

As described herein, in some embodiments, the fluid collection device comprises a bottom portion. The bottom portion may have any suitable shape for receiving a fluid. In some embodiments, the bottom portion has a concave shape. For example, as shown in FIGS. 2A-2C, bottom portion 225 is concave and rounded. In some embodiments, the shape of the bottom portion may be rounded, square, beveled, or funnel-like (e.g., at least partially conical). Other shapes are also possible. The bottom portion may include one or more channels (e.g., for transferring a fluid) as described herein.

As described herein, the fluid collection device may include one or more channels (e.g., microfluidic channels) connected thereto. In some embodiments, the channel is integrally connected to and in fluidic communication with the fluid collection region. The channels may, for example, facilitate transfer of fluid from the fluid collection device to a secondary channel or device. In certain embodiments, a channel described herein is a receiving channel that can receive a secondary channel for fluid transfer.

In some embodiments, referring again to FIG. 1H, fluid collection region 105 may be designed to have a critical volume greater than the volume of fluid path inlet 129 (or the fluid path itself). For example, fluid collection region 105 may be configured and arranged such that multiple fluid path inlets may be inserted and removed (e.g., sequentially) such that at least a portion of the fluid 150 may be transferred from the fluid collection region to more than one (e.g., two or more, three or more, four or more, five or more) fluid path inlets. In an exemplary embodiment, a fluid is introduced to fluid collection region 105 and, upon reaching a sufficient volume of fluid (e.g., a volume greater than the critical volume of fluid collection region 105), at least a portion of the fluid flows into a first fluid path inlet (e.g., a first fluid path inlet inserted into channel 130). The first fluid path inlet may be removed from the receiving channel (e.g., after filling of the first fluid path inlet with at least a portion of the fluid) and, in some embodiments, a second fluid path inlet may be inserted into the receiving channel such at least a portion of the fluid (e.g., fluid 150) remaining in fluid collection region 105 is transferred to the second fluid path inlet. In some embodiments, channel 130 and/or fluid collection region 105 are configured and arranged such that, after removal of the first fluid path inlet, fluid 150 does not substantially leak from the fluid collection region and/or into the receiving channel (e.g., the fluid does not leak into channel 130 in the absence of a fluid path inlet present within the channel). The first and second fluid path inlets may be used to introduce the fluid into a fluidic device described herein (e.g., a microfluidic device), or multiple fluidic devices.

In some embodiments, a channel of the fluid collection device (e.g., in fluidic communication with the fluid collection region) has a particular length. In certain embodiments, the length of the channel includes any shaped portions such as concave portions (e.g., concave portion 232 in FIGS. 2B-2C). In some embodiments, the length of the channel is greater than or equal to 1 mm, greater than or equal to 2 mm, greater than or equal to 3 mm, greater than or equal to 5 mm, greater than or equal to 7 mm, or greater than or equal to 9 mm. In certain embodiments, the length of the channel is less than or equal to 10 mm, less than or equal to 9 mm, less than or equal to 7 mm, less than or equal to 5 mm, less than or equal to 3 mm, or less than or equal to 2 mm. Combinations of the above-referenced ranges are also possible (e.g., greater than or equal to 1 mm and less than or equal to 10 mm). Other ranges are also possible. In embodiments in which more than one channel is associated with the fluid collection device, each channel may independently have a length in one or more of the above-referenced ranges.

A channel of the fluid collection device (e.g., a channel integrally connected to and/or in fluidic communication with the fluid collection region) may have any suitable average inner cross-sectional dimension. The inner cross-sectional dimension (e.g., an inner diameter) of the channel is measured perpendicular to the direction of fluid flow. In some embodiments, the average inner cross-sectional dimension of the channel is less than or equal to 5 mm, less than or equal to 4 mm, less than or equal to 3 mm, less than or equal to 2 mm, less than or equal to 1 mm, less than or equal to 0.5 mm, less than or equal to 0.3 mm, or less than or equal to 0.2 mm. In certain embodiments, the average inner cross-sectional dimension of the channel is at least 0.1 mm, at least 0.2 mm, at least 0.3 mm, at least 0.5 mm, at least 1 mm, at least 2 mm, at least 3 mm, or at least 4 mm. Combinations of the above-referenced ranges are also possible (e.g., at least 0.1 mm and less than or equal to 5 mm). Other ranges are also possible. In embodiments in which more than one channel is associated with the fluid collection device, each channel may independently have an average inner cross-sectional dimension in one or more of the above-referenced ranges.

As described herein, in some embodiments, a channel of the fluid collection device (e.g., a receiving channel) includes a concave portion. For example, referring again to FIG. 1C, channel 130 comprises a concave portion 132. In some embodiments, at least a portion of the channel (e.g., receiving channel) is configured and arranged to receiving a secondary channel, such as a fluidic channel of a fluidic connector or other fluidic device. The concave portion may, in some cases, assist in the alignment and/or receiving of the secondary channel, such as the fluidic channel of a fluidic connector. For example, in certain embodiments, at least a portion of a surface of a fluidic channel of a fluidic connector may be contacted with a surface of the concave portion such that the concave portion guides the fluidic channel into the channel of the fluid collection device. The concave portion may have any suitable cross-sectional shape (e.g., rounded, square, beveled, conical).

In some embodiments, the bottom portion of the sidewall (e.g., bottom portion 125 of sidewall 120 in FIG. 1C) comprises a first opening 134 that is fluidically connected to channel 130 and the channel has a second opening 136 having a diameter greater than the diameter of the first opening. In certain embodiments, the diameter of the first opening and the diameter of the second opening are equal; however, other ratios are also possible. For example, in some embodiments, the ratio of the diameter of the second opening to the first opening is greater than or equal to 1, greater than or equal to 1.25, greater than or equal to 1.5, greater than or equal to 1.75, greater than or equal to 2, greater than or equal to 2.5, greater than or equal to 3, greater than or equal to 4, or greater than or equal to 5. In certain embodiments, the ratio of the diameter of the second opening to the first opening is less than or equal to 10, less than or equal to 5, less than or equal to 4, less than or equal to 3, less than or equal to 2.5, less than or equal to 2, less than or equal to 1.75, less than or equal to 1.5, or less than or equal to 1.25. Combinations of the above-referenced ranges are also possible (e.g., greater than or equal to 1 and less than or equal to 10). Other ranges are also possible. In some embodiments, the second opening (e.g., comprising a portion of the concave portion) is configured and arranged to receive a secondary channel such as a fluidic channel of a fluidic connector.

The fluid collection device or any portion of the fluid collection device (e.g., the fluid collecting region, the edge, the tapered edge, the sidewall, the bottom portion) may be made from any suitable material. Non-limiting examples of suitable materials include polycarbonate, copolymers of styrene and butadiene, polyethylene (e.g., low density polyethylene, high density polyethylene), polypropylene, polyvinyl chloride, polystyrene, polytetrafluoroethylene, polyurethane, poly(methyl methacrylate), acrylonitrile butadiene styrene, polylactic acid, poly ether ketone, polyetherimide, polyphenylene oxide, and polyethylene terephthalate. Other materials are also possible. In some cases, the material may be biocompatible. In certain embodiments, the material may comprise one or more additives. In some embodiments, the additive may change the surface energy of the material (e.g., such that the material is hydrophobic, such that the material is hydrophilic) relative to the surface energy of the material without the additive. The additive may be present in any suitable amount (e.g., between 0.1 wt % and 20 wt % of the combined weight of the material).

In some embodiments, a portion of the fluid collection device (e.g., at least a portion of the edge (e.g., tapered edge), the sidewall, the bottom portion, and/or the receiving channel) may comprise a treated surface. For instance, all or portions of a surface may be treated to modify a physical and/or chemical property of the surface. In some embodiments, at least a portion of the fluid collection device is coated with a chemical or biological reagent (e.g., a small molecule or a biomolecule). Non-limiting examples of suitable small molecules include anticoagulants (e.g., EDTA, citrate), detergents (e.g., sodium dodecyl sulfate, sodium decyl sulfate, Tween™-20, Tween™-40, Tween™-80, fluorinated detergents such as Capstone® FS-50 and FS-51, perfluorohexanoic acid, perfluorooctanoic acid), solubilization agents (e.g., beta-cyclodextrin, beta-cyclodextrin derivatized with functional groups such as methyl-, hydroxyethyl-, and hydroxypropyl-), and pH buffers (e.g., acetate, citrate, ACES, borate, tetraborate, carbonate buffers). Non-limiting examples of suitable biomolecules include (anti-) coagulant (e.g., heparin, coagulations factor) and, proteins (e.g., mouse IgG, antibodies, protein conjugates, bovine serum albumin). In some embodiments, at least a portion of the fluid collection device is coated such that the portion of the fluid collection device is hydrophilic or hydrophobic. Those skilled in the art would be capable of selecting suitable methods for making a surface hydrophilic or hydrophobic including, but not limited to, chemical functionalization. In some embodiments, at least a portion of the fluid collection device is treated with corona/plasma treatment and/or coated with a particular molecule or functionality (e.g., amine, carboxylic acid, silane).

At least a portion of the fluid collection device (e.g., at least a portion of the edge, the tapered edge, the sidewall, the bottom portion, and/or the receiving channel) may have a particular root mean square (RMS) surface roughness. In certain embodiments, the RMS surface roughness may be, for example, less than or equal to about 5 microns, less than or equal to about 3 microns, less than or equal to about 1 micron, less than or equal to about 0.8 microns, less than or equal to about 0.5 microns, less than or equal to about 0.3 microns, less than or equal to about 0.1 microns, less than or equal to about 0.08 microns, less than or equal to about 0.05 microns, less than or equal to about 0.08 microns, less than or equal to about 0.01 microns, or less than or equal to about 0.005 microns. In some instances, the RMS surface roughness may be greater than or equal to about 0.005 microns, greater than or equal to about 0.01 microns, greater than or equal to about 0.05 microns, greater than or equal to about 0.1 microns, greater than or equal to about 0.5 microns, greater than or equal to about 1 micron, or greater than or equal to about 3 microns. Combinations of the above-referenced ranges are also possible (e.g., greater than or equal to about 0.05 microns and less than or equal to about 5 microns, greater than or equal to about 0.05 microns and less than or equal to about 1 micron). In some embodiments, surfaces that are configured to contact a fluid (e.g., a surface of the fluid collection region) may have a surface roughness ranging between about 0.05 and 0.1 microns. RMS surface roughness is a term known to those skilled in the art, and may be expressed as:

$$\sigma_h = [\langle (z - z_m)^2 \rangle]^{1/2} = \left[ \frac{1}{A} \int_A (z - z_m)^2 dA \right]^{1/2}$$

where A is the surface to be examined, and $|z-z_m|$ is the local height deviation from the mean. RMS surface roughness, as described herein, may be determined using profilometry.

In general, the roughness of a surface may be formed during fabrication or later modified using any suitable method. Exemplary methods of fabricating or modifying the surface roughness include chemical etching (e.g., acid, alkaline, corrosive solvent), plasma etching (e.g., low pressure, atmospheric, flame, plasma etching with inert and/or reactive gases), electrochemical etching, corona discharge, mechanical methods (e.g., mechanical machining, laser machining, mechanical polishing, mechanical grinding, bead-blasting, grit-blasting, shot-peening), ultrasonic machining, electrical methods (e.g., electrochemical polishing, electric discharge machining, electroforming), coating (e.g., by spray-coating, physical vapor deposition, chemical vapor deposition, painting), and combinations thereof. In some instances, the surface roughness may be produced using a molding process. The surface roughness of the mold may be modified using any of the above methods and/or coating or plating the mold surface. Other methods of producing a desired surface roughness are also possible.

In some embodiments, at least a portion of the fluid collection device may have a particular wettability (e.g., of at least about 20 dynes/cm and less than or equal to about 60 dynes/cm). In some embodiments, at least a portion of the fluid collection device has a wettability of at least 20 dynes/cm, at least 25 dynes/cm, at least 30 dynes/cm, at least 35 dynes/cm, at least 40 dynes/cm, at least 42 dynes/cm, at least 45 dynes/cm, at least 50 dynes/cm, at least 55 dynes/cm, or at least 56 dynes/cm. In certain embodiments, at least a portion of the fluid collection device has a wettability of less than or equal to 60 dynes/cm, less than or equal to 56 dynes/cm, less than or equal to 55 dynes/cm, less than or equal to 50 dynes/cm, less than or equal to 45 dynes/cm, less than or equal to 42 dynes/cm, less than or equal to 40 dynes/cm, less than or equal to 35 dynes/cm, less than or equal to 30 dynes/cm, or less than or equal to 25 dynes/cm. Combinations of the above-referenced ranges are also possible (e.g., at least 20 dynes/cm and less than or equal to 60 dynes/cm, at least 35 dynes/cm and less than or equal to 42 dynes/cm, at least 20 dynes/cm and less than or equal to 56 dynes/cm). Other ranges are also possible. Wettability, as described herein, may be determined by contact angle goniometry.

Figure 3A:
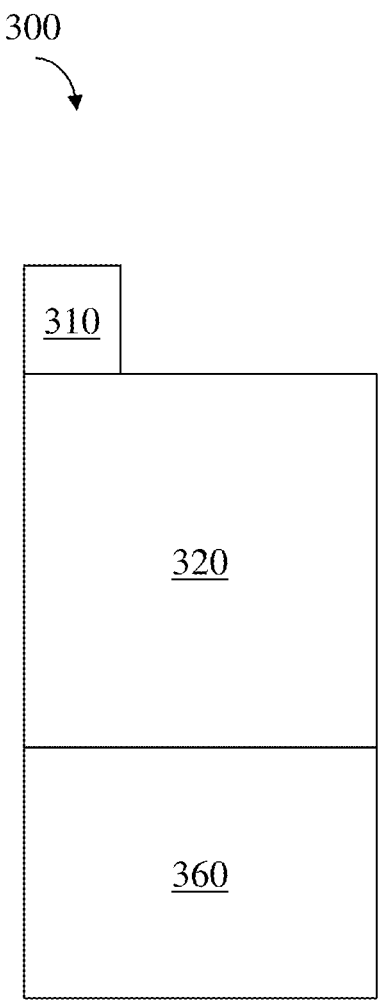
FIG. 3A is a schematic drawing of a fluid collection device and a fluidic connector, according to one set of embodiments.

As described herein, in some embodiments, a fluid collection device comprising a fluid collection region can facilitate introduction of a fluid into a secondary vessel for containing at least a portion of the fluid, such as a device, adapter, channel, container, or fluidic connector. For example, referring FIG. 3A, a system 300 comprises a fluid collection device comprising an edge 310 and a sidewall 320. The fluid collection device may facilitate the transfer of a fluid into a vessel 360. In some embodiments, the vessel is a container such as a vial. The vessel may be contacted with or be connected with the fluid collection device (e.g., at a receiving channel of the fluid collection device). Such contact may be reversible or irreversible.

Figure 3B:
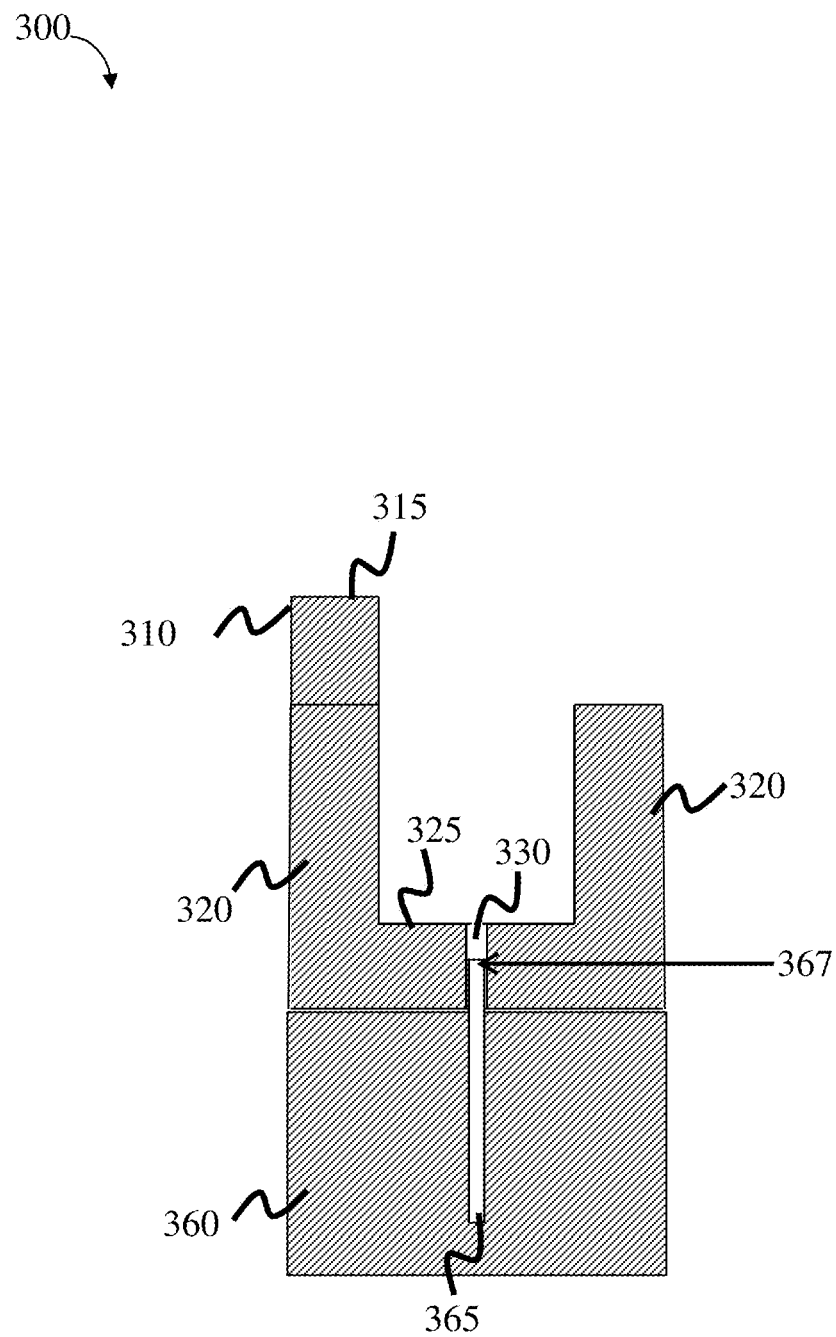
FIG. 3B is a cross-sectional schematic drawing of a fluid collection device and a fluidic connector, according to one set of embodiments.

In some embodiments, the vessel is a fluidic connector (i.e., a fluidic device that comprises a fluidic channel). In some embodiments, the fluidic connector may serve as an adapter for a fluidic system, as described in more detail herein. In certain embodiments, the fluidic connector includes a fluid path having a fluid path inlet and a fluid path outlet. In some such embodiments, the fluidic channel (or fluid path) is adapted and arranged to connect to the fluid collection device (e.g., at the receiving channel). Referring now to FIG. 3B, in some embodiments, a system 300 comprises a fluid collection device comprising an edge 310 (with an edge surface 315, optionally tapered), a sidewall 320, a bottom portion 325, and a receiving channel 330. In some such embodiments, system 300 further comprises a fluidic connector 360 (e.g., a secondary fluidic device) comprising a fluidic channel 365. In certain embodiments, the receiving channel (receiving channel 330) of the fluid collective device is configured to receive the fluidic channel (fluidic channel 365) of the fluidic connector. For instance, the fluidic channel of the fluidic connector may be a tube or channel that extends from the fluidic connector. In some such embodiments, the fluidic channel of the fluidic connector may be at least partially disposed within, and in fluidic connection with, the receiving channel of the fluid collection device. In some embodiments, upon connection of the fluid collection device and the fluidic connector, the fluidic channel of the fluidic connector extends beyond the bottom portion (e.g., bottom portion 325) of the fluid collection device. For example, the fluidic channel of the fluidic connector may traverse the entire length of the receiving channel, and extend beyond the receiving channel and the bottom portion of the fluid collection device, such that it protrudes upwards into the fluid collection region. In certain embodiments, the fluidic channel may be reversibly attached to the receiving channel.

In some embodiments, a fluid (e.g., sample or reagent) introduced into the fluid collection device may be transferred (e.g., upon reaching a certain volume as described above) into the receiving channel and/or the fluidic channel disposed within the receiving channel.

Figure 4A:
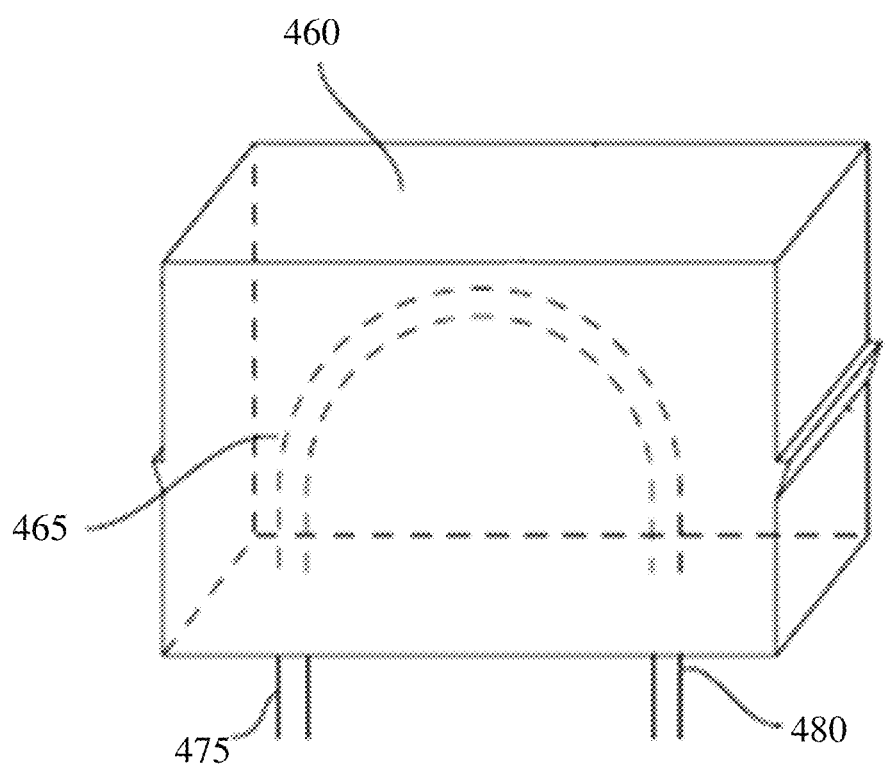
FIG. 4A is a top perspective view of a fluidic connector, according to one set of embodiments.

The fluidic channel of a fluidic connector may comprise a fluid path inlet and a fluid path outlet. For example, as shown illustratively in FIG. 4A, a fluidic connector 460 comprises fluidic channel 465 having a fluid path inlet 475 and fluid path outlet 480. In certain embodiments, the fluid path inlet connects to the receiving channel of the fluid collection device. In some such embodiments, upon connection of the fluid collection device and the fluidic connector, the fluid path inlet of the fluidic connector connects to the receiving channel of the fluid collection device to allow fluid communication between the fluidic connector and the fluid collection device. In some embodiments, upon connection of the fluid collection device and the fluidic connector, the fluid path inlet of the fluidic connector extends beyond the bottom portion of the fluid collection device. For example, the fluidic channel of the fluidic connect may traverse the entire length of the receiving channel, and extend beyond the receiving channel and the bottom portion of the fluid collection device, such that it protrudes upwards into the fluid collection region. In certain embodiments, the fluidic channel is a capillary tube.

Fluidic connectors and components thereof are described in more detail, for example, in U.S. Pat. No. 8,202,492, issued Jun. 19, 2012 (filed May 1, 2008) and entitled "Fluidic Connectors and Microfluidic Systems", which is incorporated herein by reference in its entirety for all purposes.

The fluidic channel of a fluidic connector may have any suitable average inner cross-sectional dimension (e.g., average inner diameter of the fluid path). In some embodiments, the average inner cross-sectional dimension of the fluidic channel is less than or equal to 5 mm, less than or equal to 4 mm, less than or equal to 3 mm, less than or equal to 2 mm, less than or equal to 1 mm, less than or equal to 0.5 mm, less than or equal to 0.3 mm, or less than or equal to 0.2 mm. In certain embodiments, the average inner cross-sectional dimension of the fluidic channel is at least 0.1 mm, at least 0.2 mm, at least 0.3 mm, or at least 0.5 mm, at least 1 mm, at least 2 mm, at least 3 mm, or at least 4 mm. Combinations of the above-referenced ranges are also possible (e.g., at least 0.1 mm and less than or equal to 5 mm). Other ranges are also possible.

In some embodiments, the ratio of the average inner cross-sectional dimension of the fluidic channel and the average inner cross-sectional dimension of the receiving channel is less than 100, less than 50, less than 25, less than 20, less than 10, less than 5, less than 4, less than 2, less than 1.5, or less than 1.2. In certain embodiments, the ratio of the average inner cross-sectional dimension of the fluidic channel and the average inner cross-sectional dimension of the receiving channel is greater than or equal to 1.1, greater than or equal to 1.2, greater than or equal to 1.5, greater than or equal to 2, greater than or equal to 4, greater than or equal to 5, greater than or equal to 10, greater than or equal to 20, greater than or equal to 25, or greater than or equal to 50. Combinations of the above-referenced ranges are also possible (e.g., greater than or equal to 1.1 and less than 100, greater than or equal to 1.1 and less than 25). Other ranges are also possible.

In certain embodiments, the ratio of the outer cross-sectional dimension of the fluid path inlet of the fluidic connector and the inner cross-sectional dimension of the receiving channel (e.g., measured at opening 134 shown in FIG. 1C) of the fluid collection device is between about 1:1.01 and about 1:1.25 For example, referring again to FIG. 3B, the ratio of the inner cross-sectional dimension of receiving channel 330 and the outer cross-sectional dimension of fluidic channel 365 (measured at fluid path inlet 367 of fluidic channel 365) may be between about 1:1.01 and about 1:1.25. In some embodiments, the ratio of the outer cross-sectional dimension of the fluid path inlet and the inner cross-sectional dimension of the receiving channel is less than or equal to about 1:1.01, less than or equal to about 1:1.02, less than or equal to about 1:1.05, less than or equal to about 1:1.07, less than or equal to about 1:1.09, less than or equal to 1:1.1, less than or equal to 1:1.25, or less than or equal to about 1:1.5. In certain embodiments, the ratio of the outer cross-sectional dimension of the fluid path inlet and the inner cross-sectional dimension of the receiving channel is at least about 1:1.5, at least about 1:1.25, at least about 1:1.1, at least about 1:1.09, at least about 1:1.07, at least about 1:1.05, or at least about 1:1.02. Combinations of the above-referenced ranges are also possible (e.g., at least about 1:1.1 and less than or equal to about 1:1.01). Other ranges are also possible.

A fluidic channel of the fluidic connector (or of a vessel) may have any suitable volume. In certain embodiments, the volume of the fluidic channel is less than or equal to 50 microliters, less than or equal to 40 microliters, less than or equal to 30 microliters, less than or equal to 20 microliters, less than or equal to 18 microliters, less than or equal to 16 microliters, less than or equal to 14 microliters, less than or equal to 12 microliters, less than or equal to 10 microliters, less than or equal to 5 microliters, less than or equal to 2 microliters, or less than or equal to 1 microliter. In certain embodiments, the volume of the fluidic channel is at least 0.1 microliters, at least 0.5 microliters, at least 1 microliter, at least 2 microliters, at least 5 microliters, at least 10 microliters, at least 12 microliters, at least 14 microliters, at least 16 microliters, at least 18 microliters, at least 20 microliters, at least 30 microliters, or at least 40 microliters. Combinations of the above-referenced ranges are also possible (e.g., at least 0.1 microliters and less than or equal to 20 microliters). Other ranges are also possible.

In some embodiments, the fluid collection device may comprise one or more additional components (e.g., fluidic features, non-fluidic features) which form one or more additional connections or attachment points between the fluid collection device and the vessel to which the fluid collection device connects (e.g., fluidic connector). In certain embodiments, the fluid collection device comprises at least one fluidic feature complementary to the fluid path outlet of the fluidic connector so as to form a fluidic connection between the fluid path outlet and the fluid collection device upon connection.

In some embodiments, the fluid collection device comprises a region configured to receive at least a second portion of the fluidic channel (e.g., the fluid path outlet) of a vessel to which the fluid collection device connects (e.g., fluidic connector). Referring again to FIGS. 4B-4C, fluid collection device 401 comprises region 440 configured to receive at least a second portion of the fluidic channel (e.g., such as fluid path outlet 480 of fluidic channel 465 of fluidic connector 460, shown in FIG. 4A). Region 440 may have any suitable shape and may be configured, in some embodiments, to cover (e.g., cap) the second portion of the fluidic channel. In some such embodiments, region 440 may protect the second portion of the fluidic channel from, for example, contamination. In other embodiments, the region comprises an opening.

In certain embodiments, the fluid collection device comprises at least one non-fluidic feature complementary to a non-fluidic feature of the vessel to which the fluid collection device connects (e.g., fluidic connector). In some such embodiments, the non-fluid feature of the fluid collection device and the complementary non-fluidic feature of the vessel (e.g., fluidic connector) may form a non-fluidic connection between the fluidic connector and the vessel upon connection. In some cases, the non-fluidic feature(s) of the fluid collection device and/or of the vessel (e.g., fluidic connector) may guide insertion of the fluid collection device into the vessel during use. Additionally or alternatively, the non-fluidic feature(s) of the fluid collection device may facilitate attachment of the fluid collection device to the vessel during transfer of fluid from the fluid collection device to the fluidic connector.

Figure 4B:
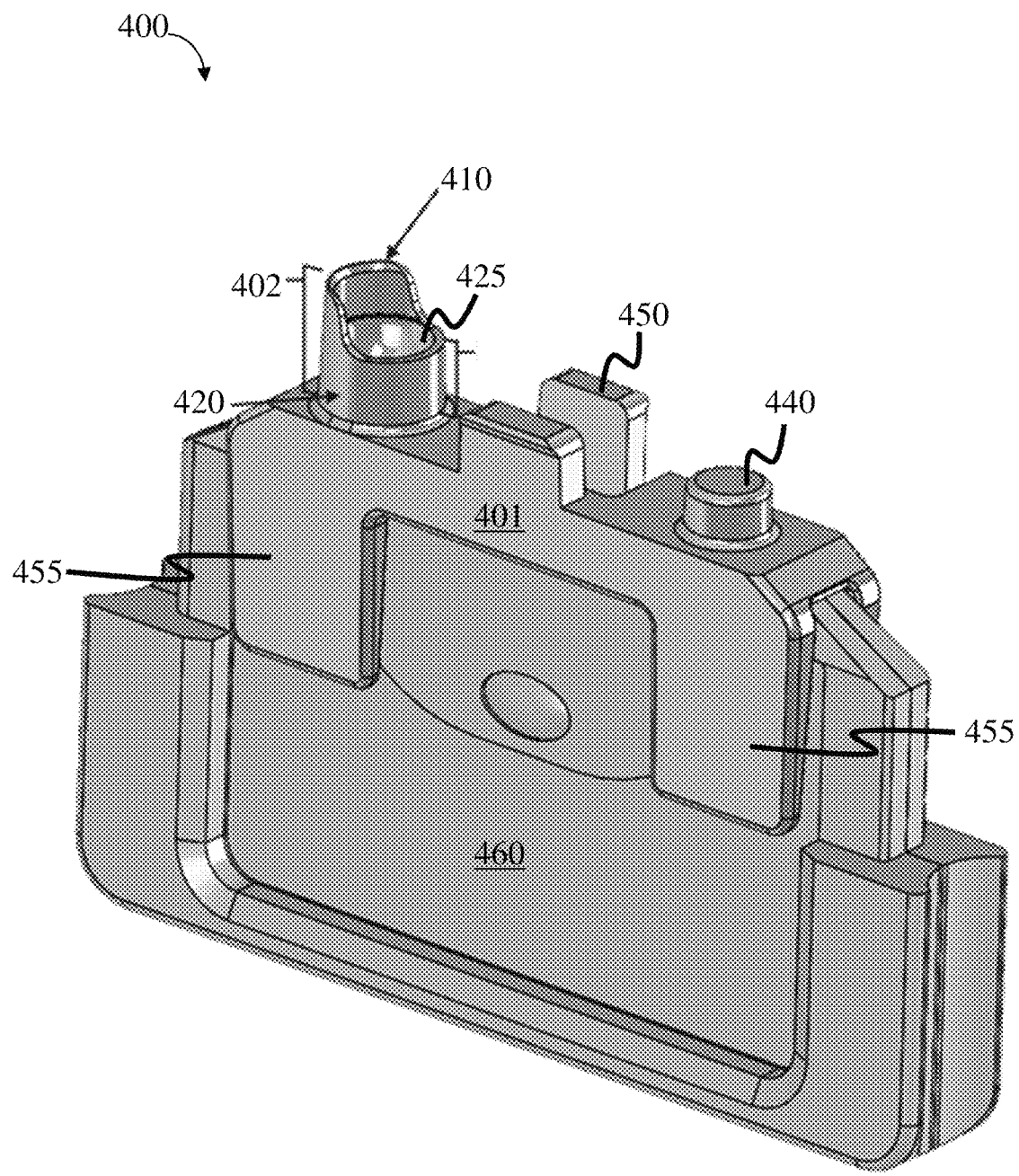
FIGS. 4B-4C are perspective view schematic drawings of a fluid collection device and fluidic connector, according to one set of embodiments.
Figure 4C:
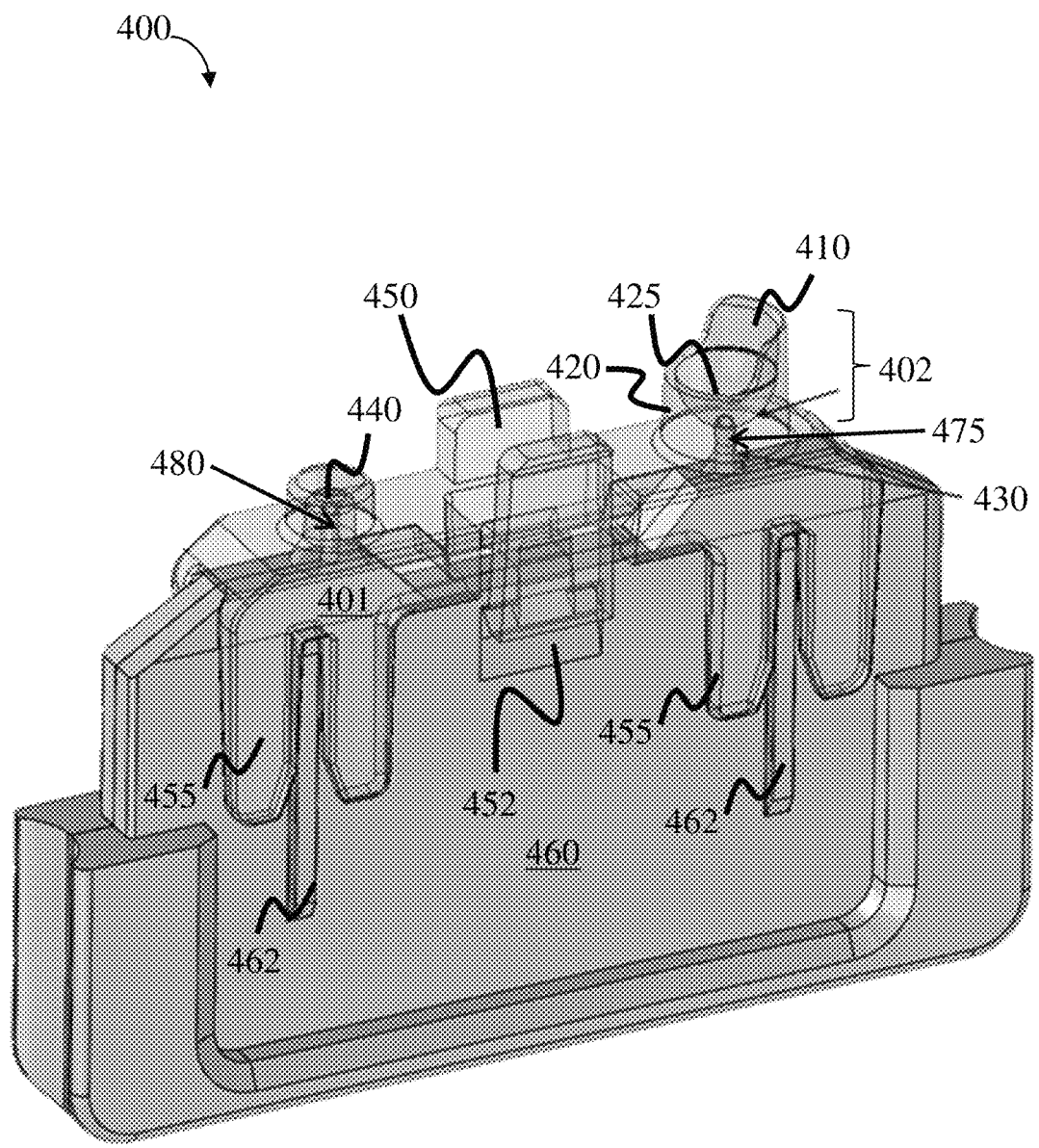

Referring now to FIGS. 4B-4C, a fluid collection device 401 comprises non-fluidic features 455 which have a shape and configuration that are complementary to the shape and configuration of non-fluidic features on fluidic connector 460. For example, as shown illustratively in FIG. 4C, fluidic connector 460 comprises rails 462 which are shaped and dimensioned to be complementary to the shape and dimension of features 455 on the fluid collection device. In some embodiments, the rail is a raised feature. In certain embodiments, the rail is an embedded feature. The rail may have any suitable shape and may be, in some cases, elongated, rounded, or square. Other shapes and configurations are also possible.

Although FIGS. 4B-4C show non-fluidic features positioned at particular locations, in other embodiments, the features can be located any suitable location on the fluidic connector and/or the fluid collection device. Furthermore, although FIGS. 4B-4C show non-fluidic features in the form of two components (e.g., rails 462), in some embodiments non-fluidic features may be in the form of a single component. In other embodiments, the non-fluidic features are in the form of more than two components.

In some embodiments, the fluid collection device and/or the fluidic connector comprises an attachment mechanism. In certain embodiments, the attachment mechanism comprises an opening configured to receive the fluidic connector. Referring again to FIG. 2C, in some embodiments, fluid collection device 200 comprises attachment mechanism 250. In certain embodiments, the attachment mechanism may connect to a complementary feature on the fluidic connector. For example, referring to FIG. 4C, fluid collection device 401 comprises attachment mechanism 450 and fluidic connector 460 comprises complementary attachment mechanism 452. Non-limiting examples of suitable attachment mechanisms include clips (and receiving portions), magnets, friction fit, or the like. Other attachment mechanisms are also possible. In certain embodiments, fluid collection device comprises an attachment mechanism comprising a hinge. The attachment mechanism may facilitate attachment of the fluid collection device to the vessel (e.g., fluidic connector) during transfer of fluid from the fluid collection device to the vessel. The attachment mechanism may be reversible to allow reversible attachment between the fluid collection device and the vessel, or irreversible to allow irreversible attachment between the fluid collection device and the vessel.

As described herein, in some embodiments, once fluid is collected using a fluid collection device, at least a portion of the fluid may be transferred to a vessel (e.g., fluidic connector). In some embodiments, at least a portion of the collected fluid is transferred to a fluidic connector, which can be connected to, and/or is part of, an analysis device. At least a portion of the fluid from the fluidic connector can then be transferred to the analysis device. In other embodiments, at least a portion of the collected fluid is transferred to an analysis device directly (e.g., a fluidic connector may be part of the analysis device directly).

An analysis device to which the vessel (fluidic connector) or fluid connection device may connect may comprise a fluidic system. In some embodiments, the fluidic system comprises at least one channel having an inlet and an outlet. In certain embodiments, a fluidic connector that contains a fluid (e.g., a sample or reagent), such as a fluid transferred to the fluidic connector by the fluid collection device, connects to the fluidic system. In certain embodiments, the fluidic connector is adapted and arranged to fasten with the fluidic system and allow fluid communication between the fluidic system and the fluidic connector. In certain embodiments, upon connection of the fluidic connector to the fluidic system, the fluid path inlet of the fluidic connector connects to an outlet of the fluidic system. In some embodiments, upon connection of the fluidic connector to the fluidic system, the fluid path outlet of the fluidic connector connects to an inlet of the fluidic system.

Figure 5A:
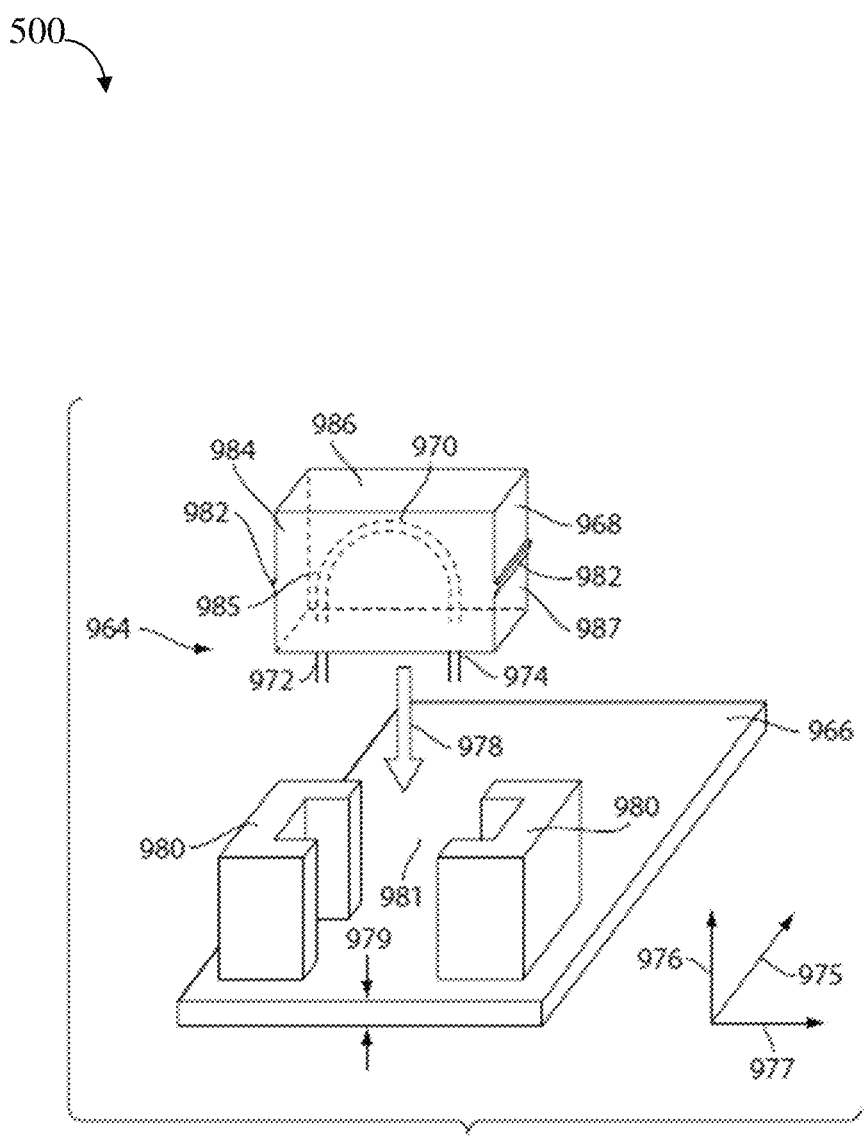
FIGS. 5A-5B are perspective view schematic drawings of a fluidic connector and a fluidic system, according to one set of embodiments.
Figure 5B:
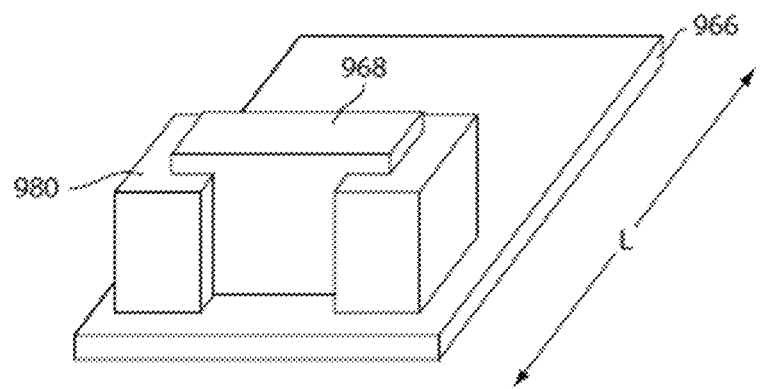

As shown illustratively in the embodiments illustrated in FIGS. 5A and 5B, device 500 may include a substrate 966, a fluidic connector 968, and an alignment element 980 (e.g., a guiding component). Substrate 966 may include a microfluidic system. The microfluidic system may comprise, for example, at least a first microfluidic channel including an inlet and an outlet and a second microfluidic channel including an inlet and an outlet (not shown). Fluidic connector 968, may have a configuration as described herein and may be constructed for matching connection to the substrate. The fluidic connector may include a fluid path 970 having a fluid path inlet 972 and a fluid path outlet 974. Upon connection of the fluidic connector to the substrate, the fluid path inlet may connect to the outlet of the first microfluidic channel of the substrate, and the fluid path outlet 974 may connect to the inlet of the second microfluidic channel of the substrate. This connection can result in fluid communication between the first and second microfluidic channels of the substrate.

As shown in the illustrative embodiments of FIGS. 5A and 5B, the device may include an alignment element 980 associated with the substrate and extending approximately perpendicular to the substrate. For example, while substrate 966 (as well as the first and second microfluidic channels) lies generally in the plane defined between arrows 975 and 977, alignment element 980 extends generally perpendicular to the substrate in the plane defined by arrows 975 and 976.

In other embodiments, the alignment element may extend approximately parallel to the substrate.

As illustrated, alignment element 980 includes a cavity 981 constructed and arranged to receive and engage the fluidic connector and thereby position the connector in a predetermined, set configuration relative to the substrate. The cavity may have a depth of, for example, at least 0.5 cm, at least 1 cm, at least 1.5 cm, at least 2 cm, at least 3 cm, or at least 4 cm (e.g., as measured from the position of the fluid path inlet and/or fluid path outlet upon engagement of the fluidic connector and the alignment element.). In some embodiments, the cavity may have a depth of less than or equal to 5 cm, less than or equal to 4 cm, less than or equal to 3 cm, less than or equal to 2 cm, less than or equal to 1.5 cm, or less than or equal to 1 cm. Combinations of the above-referenced ranges are also possible (e.g., at least 0.5 cm and less than or equal to 5 cm). Other ranges are also possible. The cavity may have a depth similar or equal to the height of the fluidic connector. The cavity does not necessarily have to encompass all sides of the fluidic connector, as long as it is constructed and arranged to receive and engage the fluidic connector and thereby position the connector in a predetermined, set configuration relative to the substrate.

In some embodiments, the configuration of a cavity and/or an engaging surface of an alignment element causes the fluid path of the fluid connector to lie approximately perpendicular to the substrate (and, therefore, approximately perpendicular to the microfluidic channels within the substrate). For example, as illustrated in FIGS. 5A and 5B, fluid path 970 is approximately perpendicular to the substrate in the plane defined by arrows 975 and 976. In other embodiments, a fluid path of the fluid connector lies at an angle between 90 and 180 degrees or between 0 and 90 degrees relative to the substrate.

Although FIGS. 5A and 5B show alignment element 980 positioned at one end of the substrate, in other embodiments, an alignment component can extend along the length, L, of the substrate, e.g., towards opposing ends of the substrate. For example, the alignment component may be a block having a length and width similar to that of the substrate, but may include a cavity where the fluidic connector is to be inserted. Furthermore, although FIGS. 5A and 5B show alignment element 980 in the form of two components, in some embodiments an alignment element may be in the form of a single component. In other embodiments, the alignment element is in the form of more than two components.

A fluidic connector and/or a fluidic system can be fabricated of any material suitable for forming a channel. Non-limiting examples of materials include polymers (e.g., polyethylene, polystyrene, polycarbonate, poly(dimethylsiloxane), and a cyclo-olefin copolymer (COC)), glass, quartz, and silicon. Those of ordinary skill in the art can readily select a suitable material based upon e.g., its rigidity, its inertness to (e.g., freedom from degradation by) a fluid to be passed through it, its robustness at a temperature at which a particular device is to be used, and/or its transparency/opacity to light (e.g., in the ultraviolet and visible regions). In some embodiments, the material and dimensions (e.g., thickness) of a substrate are chosen such that the substrate is substantially impermeable to water vapor.

In some instances, a fluidic connector and/or fluidic system is comprised of a combination of two or more materials, such as the ones listed above. For instance, the channels of the device may be formed in a first material (e.g., poly(dimethylsiloxane)), and a cover that is formed in a second material (e.g., polystyrene) may be used to seal the channels. In another embodiment, a channel of the device may be formed in polystyrene or other polymers (e.g., by injection molding) and a biocompatible tape may be used to seal the channels. A variety of methods can be used to seal a microfluidic channel or portions of a channel, including but not limited to, the use of adhesives, gluing, bonding, welding, or by mechanical methods (e.g., clamping).

The articles, components, systems, and methods described herein may be combined with those described in International Patent Publication No. WO2005/066613 (International Patent Application Serial No. PCT/US2004/043585), filed Dec. 20, 2004 and entitled "Assay Device and Method"; International Patent Publication No. WO2005/072858 (International Patent Application Serial No. PCT/US2005/003514), filed Jan. 26, 2005 and entitled "Fluid Delivery System and Method"; International Patent Publication No. WO2006/113727 (International Patent Application Serial No. PCT/US06/14583), filed Apr. 19, 2006 and entitled "Fluidic Structures Including Meandering and Wide Channels"; U.S. Pat. No. 8,202,492, issued Jun. 19, 2012 (filed May 1, 2008) and entitled "Fluidic Connectors and Microfluidic Systems"; U.S. Patent Publication No. 2009/0075390, filed Aug. 22, 2008, entitled "Liquid Containment for Integrated Assays"; U.S. Pat. No. 8,222,049, issued Jul. 17, 2012 (filed Apr. 25, 2008), entitled "Flow Control in Microfluidic Systems"; U.S. Pat. No. 8,221,700, issued Jul. 17, 2012 (filed Feb. 2, 2010), entitled "Structures for Controlling Light Interaction with Microfluidic Devices"; U.S. Patent Publication No. 2010/0158756, filed Dec. 17, 2009, entitled "Reagent Storage in Microfluidic Systems and Related Articles and Methods"; U.S. Patent Publication No. 2011/0120562, filed Nov. 24, 2010, entitled "Fluid Mixing and Delivery in Microfluidic Systems"; U.S. Patent Publication No. 2011/0253224, filed Apr. 15, 2011, entitled "Feedback Control in Microfluidic Systems,"; U.S. Patent Publication No. 2011/0256551, filed Apr. 15, 2011, entitled "Systems and Devices for Analysis of Samples"; U.S. Patent Publication No. 2014/0272935, filed Feb. 7, 2014, entitled "Mixing of Fluids in Fluidic Systems"; U.S. Patent Publication No. 2013/0273643, filed Mar. 5, 2013, entitled "Methods and Apparatuses for Predicting Risk of Prostate Cancer and Prostate Gland Volume"; each of which is incorporated herein by reference in its entirety for all purposes.

As described herein, in some embodiments a fluid collection device may be used to collect a fluid sample from a subject or a patient. A "subject" or a "patient" refers to any mammal (e.g., a human), for example, a mammal that may be susceptible to a disease or bodily condition. Examples of subjects or patients include a human, a non-human primate, a cow, a horse, a pig, a sheep, a goat, a dog, a cat or a rodent such as a mouse, a rat, a hamster, or a guinea pig. Generally, the invention is directed toward use with humans. A patient may be a subject diagnosed with a certain disease or bodily condition or otherwise known to have a disease or bodily condition. In some embodiments, a patient may be diagnosed as, or known to be, at risk of developing a disease or bodily condition. In other embodiments, a patient may be suspected of having or developing a disease or bodily condition, e.g., based on various clinical factors and/or other data.

EXAMPLES

The following examples are intended to illustrate certain embodiments described herein, including certain aspects of the present invention, but do not exemplify the full scope of the invention.

Example 1

The following example demonstrates the use of a fluid collection device, according to some embodiments described herein.

A. Collection of Blood Directly from a Patient

Collection of blood from finger stick samples was performed with a fluidic collection device and a fluidic connector, as shown schematically in FIGS. 4B-4C (fluid collection device 401 and fluidic connector 460), using the following protocol:

1. Perform a finger stick and express a drop of blood from the patient. (Prior to performing the finger stick, the site of blood collection on the patient may be optionally cleaned/disinfected with a wipe (e.g., an isopropanol wipe, a detergent-based wipe).
2. Invert the patients hand so that the drop of blood is facing the ground.
3. When the drop was large enough (e.g., about 20 microliters) the fluid collection region of the fluid collection device was brought to the drop of blood.
4. Scrape the fluid collection device across the drop while keeping the edge of the fluid collection device in contact the skin.
   a. A channel (e.g., a capillary tube) of the fluidic connector will fill automatically when a critical volume of blood has been collected in the fluid collection device.
   b. The fluid collection region of the fluid collection device can be filled with an excess volume of blood such that the channel of the fluidic connector meters the sample.
5. When the channel is filled the user removes the fluid collection device from the fluidic connector.
   a. To remove the fluid collection device, the user squeezes the clip feature and pulls the fluid collection device off the fluidic connector.
   b. Excess blood does not leak through the receiving channel.
   c. The fluid collection device may be discarded upon removal.
6. The fluidic connector can then be connected to a cassette (microfluidic device) and inserted into an analyzer (e.g., Claros 1 Analyzer) to analyze the sample. For example, the fluidic connected may be attached to a cassette such as a Sangia™ tPSA cassettes, similar to the ones described in U.S. Patent Publication No. 2011/0256551, filed Apr. 15, 2011, entitled "Systems and Devices for Analysis of Samples," (e.g., see FIG. 22 and Example 1) and International Patent Publication No. WO2005/066613 (International Patent Application Serial No. PCT/US2004/043585), filed Dec. 20, 2004 and entitled "Assay Device and Method," which are incorporated herein by reference.

A. Collection of a Sample or Reagent from a Pipette

Operation for transfer samples/reagents may be as follows:

1. Via a pipette (of any type) collect an excess of sample or reagent.
2. Introduce the sample or reagent directly into the fluid collection region of the fluid collection device.
3. A channel (e.g., a capillary tube) of the fluidic connector fills automatically when a critical volume of sample has been collected in the fluid collection device
4. When the channel is filled the user removes the fluid collection device from the fluidic connector.
   a. To remove the fluid collection device, the user squeezes the clip feature and pulls the fluid collection device off the fluidic connector.
   b. The fluid collection device may be discarded upon removal.
5. The fluidic connector can then be connected to a cassette and inserted an analyzer analyze the sample as described above.

Example 2

The following example demonstrates filling of a fluid collection region of a fluid collection device having a critical volume, according to some embodiments.

A fluid collection device and fluidic connector, as shown schematically in FIGS. 4B-4C (fluid collection device 401 and fluidic connector 460), was used to determine the critical volume of the fluid collection region which results in filling of the channel of the fluidic connector. In addition, blood samples of two different hematocrit percentages were used to determine any influence on the critical volume due to red blood cell content.

Blood from two subjects was used for these experiments. The two samples of blood contained different hematocrit percentages (the volume percentage of red blood cells in the blood sample). For example, the normal range of hematocrit for humans (male and female) ranges from 35% (generally the lower bound for females) to 50% (generally the upper bound for males). To analyze the effects of different hematocrit percentages on how blood behaves when dispensed into the fluid collection device, one sample was selected of low hematocrit and one sample of high hematocrit. The low hematocrit blood had a red blood cell percentage of 39.2% and the high hematocrit blood was 50.6% red blood cells.

The first experiment involved dispensing droplets of blood of 10 μL increments against the side wall of the fluid collection region using a pipette. For each sample, droplets were dispensed until the blood reached the channel (a capillary tube) of the fluidic connector and resulted in a filled channel. The results are shown in Tables 1A and 1B. For both the low and high hematocrit blood, the critical volume was between 10 and 30 μL. "Leaking" occurred if the blood sample flowed out of the fluid collection region and dispensed onto the sample collection device in an uncontrolled manner due to an excess amount of sample being collected.

TABLE 1A

Critical Volume Test
(Low Hematocrit Blood - 39.2% Red Blood Cells)
Blood dispensed in incremental 10 μl
droplets until Capillary Tube is filled.

| Sample | Fill Volume (μL) | Note |
|---|---|---|
| 1 | 20 | Capillary tube started to fill after a few seconds at 20 μL. No leak. |
| 2 | 20 | Capillary tube started to fill after a few seconds at 20 μL. No leak. |
| 3 | 30 | Filled immediately at 30 μL. No leak. |

TABLE 1A-continued

Critical Volume Test
(Low Hematocrit Blood - 39.2% Red Blood Cells)
Blood dispensed in incremental 10 μl
droplets until Capillary Tube is filled.

| Sample | Fill Volume (μL) | Note |
|---|---|---|
| 4 | 30 | Filled at 30 μl, but started flowing through bottom at 20 μl. |
| 5 | 30 | Filled immediately at 30 μL. No leak. |

TABLE 1B

Critical Volume Test
(High Hematocrit Blood - 50.6% Red Blood Cells)
Blood dispensed in incremental 10 μL
droplets until Capillary Tube is filled.

| Sample | Fill Volume (μL) | Note |
|---|---|---|
| 1 | 20 | Filled immediately at 20 μL. No leak. |
| 2 | 30 | Filled immediately at 30 μL. No leak. |
| 3 | 30 | Filled immediately at 30 μL. No leak. |
| 4 | 30 | Filled immediately at 30 μL. No leak. |
| 5 | 20 | Filled immediately at 20 μL. No leak. |

Figure 6A:
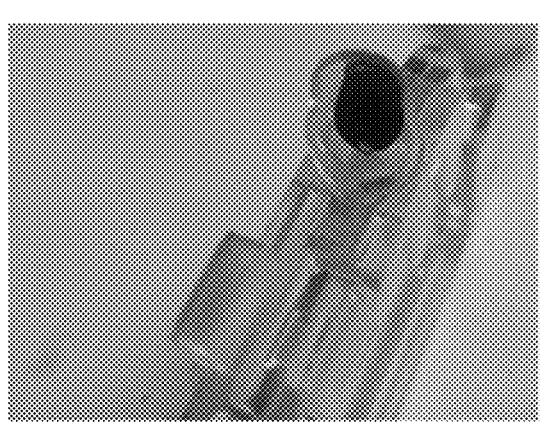
FIGS. 6A-6C are photographs of a fluid collection device, according to one set of embodiments.
Figure 6B:
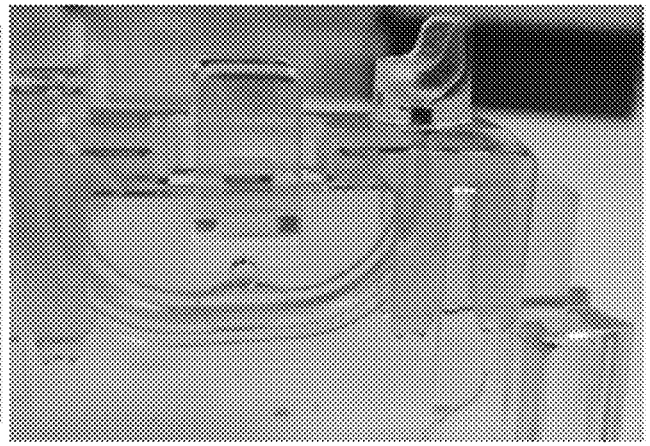
Figure 6C:
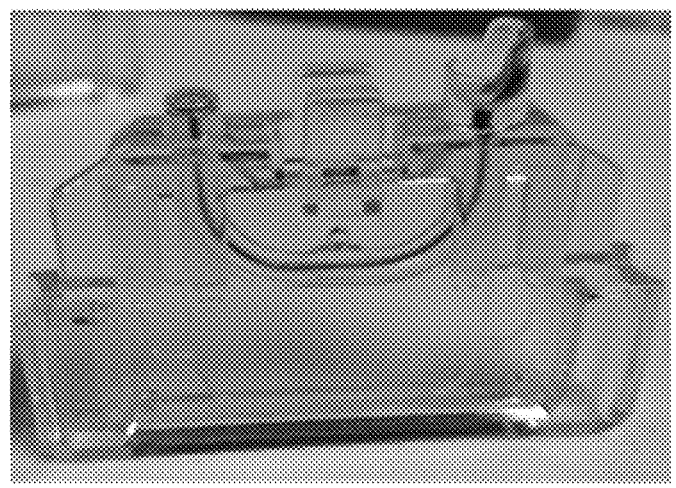

Figures demonstrating that the critical volume of the fluid collection region was not reached, and therefore did not result in filling of the channel of the fluidic connector, are shown in FIGS. 6A-6B. Figures demonstrating that the fluid collection region could be filled with a volume of sample greater than the critical holding volume, and resulting in filling of the channel of the fluidic connector, is shown in FIG. 6C.

A second experiment involved dispensing full drops of specific volumes to determine exactly how large droplets of blood would behave in the fluid collection device. Based on the previous experiment, the range between 20 μL and 30 μL was selected. The experiment was conducted by dispensing a single, full volume droplet (e.g., 20 μL, 30 μL) against the sidewall of the fluid collection region of the fluid collection device.

With respect to both low and high hematocrit blood, droplets of 22 μL were the lowest sufficient volume (i.e., critical volume) required to consistently flow and fill a capillary tube. Volumes of 22 μL, 23 μL, and 25 μL of blood for both types of blood (i.e., low and high hematocrit blood samples) resulted in a completely filled capillary tube but the time for these samples to flow and completely cover the channel opening varied. It was observed that the capillary tube filled once the opening of the tube was completely covered with the sample of blood; if the capillary tube was partially or mostly covered the sample did not flow. A droplet volume of 28 μL flowed to the tube immediately and filled immediately upon reaching the capillary tube.

A third experiment was conducted to emulate a condition where a single droplet which has insufficient volume to result in a filled capillary tube (based on the previous experiments) is dispensed and to determine how much supplemental volume would be required to induce flow. Both types of blood required a supplemental volume of 2.5 μl to induce flow when a droplet of blood of 18 μL was initially dispensed (i.e., a critical volume of 20.5 μL). When a 160 droplet of blood was dispensed of both types, a supplemental volume of 5 μL (two 2.5 μL droplets) was required to induce flow (i.e. greater than the critical volume of 20.5 μL). Once the sufficient supplemental volumes were added the blood sample immediately covered the capillary tube opening and filled the tube completely. The results are shown in Table 2.

TABLE 2

Interval Droplet Test (Low Hematocrit Blood)
An initial droplet of a specific volume is added to a blood collector.
This specific volume is known not to initiate a fill and blood is
incrementally added to replicate a situation where supplementary
blood would be added in an under fill situation.

| Sample | Initial Droplet Volume (μl) | Number of 2.5 μl Droplets Added | Total Volume | Note |
|---|---|---|---|---|
| 1 | 20 | 1 | 22.5 | Didn't fill with 20 μl droplet and filled immediately once a 2.5 μl droplet was added. |
| 2 | 18 | 1 | 20.5 | Didn't fill with 18 μl droplet and filled immediately once a 2.5 μl droplet was added. |
| 3 | 16 | 2 | 21 | Didn't fill with 16 μl droplet and filled immediately once a second 2.5 μl droplet was added. |

Interval Droplet Test (High Hematocrit Blood - 50.6% Red Blood Cells)
An initial droplet of a specific volume is added to a blood collector.
This specific volume is known not to initiate a fill and blood is
incrementally added to replicate a situation where supplementary
blood would be added in an under fill situation.

| Sample | Initial Droplet Volume (μl) | Number of 2.5 μl Droplets Added | Total Volume | Note |
|---|---|---|---|---|
| 1 | 18 | 1 | 20.5 | Didn't fill with 18 μl droplet and filled immediately once a 2.5 μl droplet was added. |
| 2 | 16 | 2 | 21 | Didn't fill with 16 μl droplet and filled immediately once a second 2.5 μl droplet was added. |

From these experiments it can be concluded that hematocrit is likely not a critical factor with respect to the behavior of a blood sample when interacting with the fluid collection region of a fluid collection device. The second experiment shows that a droplet volume of 28 μL is sufficient for initiating capillary tube filling immediately after a sample is introduced into the blood collector adaptor. It can be seen from the third experiment that if insufficient volume is introduced, once the volume is sufficient enough to initiate filling (i.e., reaches a critical holding volume) the capillary tube will fill completely.

Example 3

The following example demonstrates filling of a fluid collection region of a fluid collection device having a critical volume with a control fluid, according to some embodiments.

Example 2 characterizes the behavior of different types of blood when dispensed in various quantities into the blood collector adaptor. Since blood is a non-controllable fluid in that every sample will be different, a controlled fluid was used to confirm the critical volume of the fluid collection region. The two fluids used in these experiments were TPSA External Control—Level 2 (Lot 4131) and de-ionized water. Dye was added to the de-ionized water for the purpose of changing the color so that the liquid would be easier to see when dispensed into the blood collector adaptor. To prepare the de-ionized water for the experiments, 5 μl of methylene blue solution were added to 30 ml of de-ionized water; the methylene blue solution had a concentration of 20 mg of methylene blue per ml of de-ionized water.

The first experiment involved dispensing 100 droplets of liquid against the sidewall of the fluid collection region. For each sample, droplets were dispensed until the liquid reached the capillary tube (i.e., the fluid path inlet) inserted into the receiving channel and resulted in a filled capillary tube. The results are shown in Table 3; for both the TPSA external control and the de-ionized water 3 samples filled once a total volume of 30 μl was dispensed and two samples filled once a total volume of 20 μl was dispensed.

TABLE 3

Critical Volume Test (TPSA External Control)
TPSA control matrix dispensed in 10 μL droplets until Capillary Tube is filled.

| Sample | Fill Volume(μL) | Note |
|---|---|---|
| 1 | 30 | No Leak |
| 2 | 30 | No Leak |
| 3 | 30 | No Leak |
| 4 | 20 | No Leak |
| 5 | 20 | No Leak |

Critical Volume Test
(30 mL of DI water with 5 μL of 20 mg/mL methylene blue)
DI water dispensed in 10 μL droplets until Capillary Tube is filled.

| Sample | Fill Volume(μL) | Note |
|---|---|---|
| 1 | 20 | No Leak |
| 2 | 30 | No Leak |
| 3 | 30 | No Leak |
| 4 | 20 | No Leak |
| 5 | 30 | No Leak |

The second experiment involved dispensing full drops of specific volumes to determine exactly how large droplets of both liquids would behave in the fluid collection region. This experiment was conducted by dispensing a full volume droplet out onto the side of the dispense tip and then releasing it against the sidewall of the fluid collection region. For the TPSA External Control, a volume of 20 microliters was sufficient to result in a filled capillary tube (fluid path inlet); 24 microliters and higher resulted in an immediate fill. In the case of the de-ionized water at 21 microliters were required to generate a fill condition. Volumes of de-ionized water below 20 microliters did not result in a fill condition. Results are shown in Table 4.

TABLE 4

Large Droplet Test (TPSA External Control)

| Sample | Droplet Volume(μL) | Note |
|---|---|---|
| 1 | 25 | Filled immediately. |
| 2 | 20 | Covered capillary tube after 5 seconds and filled. |
| 3 | 16 | Did not fill |
| 4 | 18 | Filled after few minutes. |
| 5 | 19 | Did not fill. |
| 6 | 20 | Filled after 5 seconds. |
| 7 | 21 | Filled after a few seconds. |
| 8 | 22 | Filled after a few seconds. |
| 9 | 23 | Filled after a few seconds. |
| 10 | 24 | Filled immediately. |

Large Droplet Test
(30 mL of DI water mixed with 5 μL of 20 mg/mL methylene blue)

| Sample | Droplet Volume(μL) | Note |
|---|---|---|
| 1 | 20 | Filled immediately |
| 2 | 16 | did not fill |
| 3 | 17 | did not fill |
| 4 | 18 | did not fill |
| 5 | 19 | did not fill |
| 6 | 20 | did not fill |
| 7 | 21 | Filled immediately |
| 8 | 21 | Filled immediately |

A third experiment was conducted to emulate a condition where a large droplet which has insufficient volume to result in a filled capillary tube (based on the previous experiments) is dispensed and to determine how much supplemental volume would be required to induce flow. Both types of liquid required a supplemental volume of 2.50 to induce flow when 160 of liquid were initially dispensed. At 14 μl TPSA external control required 3 more droplets (7.5 μl) to initiate a fill condition and at 12 μl de-ionized water required 3 more droplets. Once the sufficient supplemental volumes were added the blood sample immediately covered the capillary tube opening and filled the tube completely. Results are shown in Table 5.

TABLE 5

Interval Droplet Test (TPSA External Control)
An initial droplet of a specific volume is added to the blood collector adaptor. This specific volume is known not to initiate a fill and liquid is incrementally added to replicate a situation where supplementary fluid would be added in an underfill situation.

| Sample | Initial Droplet Volume (μL) | Number of 2.5 μL Droplets Added | Total Volume (μL) | Note |
|---|---|---|---|---|
| 1 | 16 | 1 | 18.5 | Filled after 1 droplet added. |
| 2 | 14 | 3 | 21.5 | Filled only after 3rd droplet added. |

Interval Droplet Test (De-ionized Water)
An initial droplet of a specific volume is added to the blood collector adaptor. This specific volume is known not to initiate a fill and liquid is incrementally added to replicate a situation where supplementary fluid would be added in an underfill situation.

| Sample | Initial Droplet Volume (μL) | Number of 2.5 μL Droplets Added | Total Volume (μL) | Note |
|---|---|---|---|---|
| 1 | 20 | 1 | 22.5 | Filled after 1 droplet added. |
| 2 | 16 | 1 | 18.5 | Filled after 1 droplet added. |
| 3 | 12 | 3 | 19.5 | Filled only after 3rd droplet added. |
| 4 | 14 | 1 | 16.5 | Filled after 1 droplet added. |

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Any terms as used herein related to shape, orientation, alignment, and/or geometric relationship of or between, for example, one or more articles, structures, forces, fields, flows, directions/trajectories, and/or subcomponents thereof and/or combinations thereof and/or any other tangible or intangible elements not listed above amenable to characterization by such terms, unless otherwise defined or indicated, shall be understood to not require absolute conformance to a mathematical definition of such term, but, rather, shall be understood to indicate conformance to the mathematical definition of such term to the extent possible for the subject matter so characterized as would be understood by one skilled in the art most closely related to such subject matter. Examples of such terms related to shape, orientation, and/or geometric relationship include, but are not limited to terms descriptive of: shape—such as, round, square, circular/circle, rectangular/rectangle, triangular/triangle, cylindrical/cylinder, elliptical/ellipse, (n)polygonal/(n)polygon, etc.; angular orientation—such as perpendicular, orthogonal, parallel, vertical, horizontal, collinear, etc.; contour and/or trajectory—such as, plane/planar, coplanar, hemispherical, semi-hemispherical, line/linear, hyperbolic, parabolic, flat, curved, straight, arcuate, sinusoidal, tangent/tangential, etc.; direction—such as, north, south, east, west, etc.; surface and/or bulk material properties and/or spatial/temporal resolution and/or distribution—such as, smooth, reflective, transparent, clear, opaque, rigid, impermeable, uniform(ly), inert, non-wettable, insoluble, steady, invariant, constant, homogeneous, etc.; as well as many others that would be apparent to those skilled in the relevant arts. As one example, a fabricated article that would described herein as being "square" would not require such article to have faces or sides that are perfectly planar or linear and that intersect at angles of exactly 90 degrees (indeed, such an article can only exist as a mathematical abstraction), but rather, the shape of such article should be interpreted as approximating a "square," as defined mathematically, to an extent typically achievable and achieved for the recited fabrication technique as would be understood by those skilled in the art or as specifically described. As another example, two or more fabricated articles that would described herein as being "aligned" would not require such articles to have faces or sides that are perfectly aligned (indeed, such an article can only exist as a mathematical abstraction), but rather, the arrangement of such articles should be interpreted as approximating "aligned," as defined mathematically, to an extent typically achievable and achieved for the recited fabrication technique as would be understood by those skilled in the art or as specifically described.

What is claimed:

1. An article for introducing a fluid into a fluidic system, comprising:
   a fluid collection region comprising a substantially vertical edge having a thickness of less than or equal to 2 mm, a sidewall, and a bottom portion, wherein the fluid collection region has a holding volume of less than or equal to about 200 microliters, and a longest dimension of less than about 2 cm; and
   a channel integrally connected to and in fluidic communication with the fluid collection region, wherein the channel has an average cross sectional dimension of at least 0.1 mm and less than or equal to about 5 mm, and a length of at least about 1 mm; and
   wherein the fluid collection region is adapted and arranged to hold a fluid having a critical volume of at least 18 microliters without filling the channel, and to allow flow of the fluid into the channel when the volume of the fluid is about 25 microliters or greater without any applied positive or negative pressure.

2. An article as in claim 1, wherein the longest dimension is measured between the a furthermost internal point on the edge and a bottom-most internal point of the bottom portion.

3. An article for introducing a fluid into a fluidic system, comprising:
   a fluid collection region comprising an edge, a sidewall, and a bottom portion; and
   a receiving channel integrally connected to and in fluidic communication with the fluid collection region, wherein the receiving channel includes a concave portion adapted and arranged to reversibly connect with a fluidic channel; and
   wherein the fluid collection region is adapted and arranged to hold a fluid having a critical volume of at least 18 microliters without filling the receiving channel, and to allow flow of the fluid into the receiving channel when the volume of the fluid is about 25 microliters or greater without any applied positive or negative pressure.

4. An article for introducing a fluid into a fluidic channel, comprising: a fluid collection region comprising a curved edge, a sidewall, and a bottom portion;
   a receiving channel integrally connected to and in fluidic communication with the fluid collection region, wherein the receiving channel is adapted and arranged to be in fluidic communication and reversibly connect with a fluidic channel comprising a fluid path having a fluid path inlet and a fluid path outlet, and
   wherein the fluid collection region is adapted and arranged to hold a control fluid having a critical volume of at least 18 microliters without filling the fluidic channel, and to allow flow of the control fluid into the fluidic channel when the volume of the control fluid is about 25 microliters or greater without any applied positive or negative pressure, and wherein the control fluid is deionized water.

5. An article as in claim 3, wherein the fluidic channel is a part of a fluidic connector.

6. An article as in claim 3, wherein the edge is a curved edge.

7. An article as in claim 3, wherein the edge is tapered.

8. An article as in claim 6, wherein the edge has a radius of curvature of at least about 2 mm and less than or equal to about 10 mm.

9. An article as in claim 7, wherein the edge has a taper angle at least 0 degrees and less than 90 degrees.

10. An article as in claim 3, wherein an inner surface of the fluid collection region has an average RMS roughness of at least about 0.1 mm.

11. An article as in claim 3, wherein an inner surface of the fluid collection region has an average wettability of at least about 20 dynes/cm and less than or equal to about 56 dynes/cm.

12. An article as in claim 3, wherein at least a portion of an inner surface of the fluid collection device is coated with a biomolecule, and wherein the biomolecule is selected from the group consisting of (anti)coagulants and proteins.

13. An article as in claim 3, wherein at least a portion of an inner surface of the fluid collection region is coated with a small molecule.

14. An article as in claim 3, wherein the fluid collection region has a holding volume of between about 12 microliters and about 50 microliters.

15. An article as in claim 3, wherein the bottom portion comprises a first opening that is fluidically connected to the receiving channel, wherein the receiving channel comprises a second opening, and wherein the first opening has a diameter less than the diameter of the second opening.

16. An article as in claim 3, wherein the bottom portion has a concave shape adapted and arranged to receive a fluid.

17. An article as in claim 3, wherein the fluidic channel is a capillary tube.

18. An article as in claim 3, wherein the ratio of the inner diameter of the receiving channel and the outer diameter of the fluidic channel is less than 1.2:1.

19. An article as in claim 3, wherein the fluidic channel has a largest cross-sectional dimension of less than or equal to about 1 mm.

20. An article as in claim 3, wherein upon connection of the fluid collection region and the fluidic channel, the fluid path inlet of the fluidic channel extends beyond the bottom portion of the fluid collection region.

* * * * *